United States Patent [19]
Kraus et al.

[11] Patent Number: 5,958,768
[45] Date of Patent: Sep. 28, 1999

[54] CHIMERIC ANTIVIRAL AGENTS COMPRISING REV BINDING NUCLEIC ACIDS AND TRANS-ACTING RIBOZYMES, AND MOLECULES ENCODING THEM

[75] Inventors: Gunter Kraus, Miami, Fla.; Flossie Wong-Staal; Mang Yu, both of San Diego, Calif.; Osamu Yamada, Kobe, Japan

[73] Assignee: The Regents of the University of California, Oakland, Calif.

[21] Appl. No.: 08/697,324

[22] Filed: Aug. 23, 1996

Related U.S. Application Data

[60] Provisional application No. 60/002,793, Aug. 25, 1995.

[51] Int. Cl.$^6$ .............................. C07H 21/04; C12N 5/16; C12N 5/22; C12N 15/79; C12N 15/85
[52] U.S. Cl. .................................... 435/372.3; 435/320.1; 435/325; 435/366; 435/455; 536/24.5
[58] Field of Search .......................... 536/24.5; 435/325, 435/320.1, 366, 372.3, 455; 514/44

[56] References Cited

PUBLICATIONS

Yu, et al., Gene Therapy (1994) 1:13–26.
Yamada, et al., Gene Therapy (1994) 1:38–45.
Leavitt, et al., Hum. Gene Ther. (1994) 5:1115–1120.
Yu, et al., Virology (1995) 206:381–386.
Wong–Staal, et al. (1991) Viral and Cellular Factors that Bind to the Rev Response Element in *Genetic Structure and Regulation of HIV* (Haseltine and Wong–Staal eds; part of the Harvard AIDS Institute Series on Gene Regulation of Human Retroviruses, vol. 1), pp. 311–322.
Coffin, J.M. Science (1995) 267:483–489.
Ho, et al., Nature (1995) 373:123–6.
Wei, et al., Nature (1995) 373:117–22.
Bordignon, et al., Hum Gene Ther. (1993) 4:513–20.
Yamada, et al., Virology (1994) 205:121–126.
Yu, et al., Proc. Natl. Acad. Sci. USA (1993) 90:6340–6344.
Yu, et al., Proc. Natl. Acad. Sci. USA (1995) 92:699–703.
Feinberg, et al., Cell (1986) 46:807–817.
Malim, et al., Nature (1989) 338:254–257.
Vaishnav, et al., New Biol. (1991) 3:142–150.
Bertrand, et al., Embo J. (1994) 13:2904–12.
Luznik, et al., AIDS Res. Hum. Retrovirus (1995) 11:795–804.
Dropulic, et al. Journal of Virology (1992) 66(3):1432–1441.
Castanotto, et al. Advances in Pharmacology Academic Press (1994) 25:289–317.
Herskowitz, Nature (1987) 329:212.
Baltimore, Nature (1988) 335:395.
Ojwang, et al., Proc. Nat'l. Acad. Sci., USA (1992) 89:10802–06.
Yamada, et al. Journal of Virology (1996) 70(3):1596–1601.
Yuyama, et al. Nucleic Acids Res. (1994) 22(23):5060–5067.
Burke JM. "Clearing the way for ribozymes." Nature Biotechnology 15:414–415, 1997.
Stull RA, et al. "Antigene, ribozyme and aptamer nucleic acid drugs: Progress and prospects." Pharmaceutical Res. 12: 465–483, 1995.
Malim MH, et al. "HIV–1 structural gene expression requires binding of the Rev trans–activator to its RNA target sequence." Cell 60: 675–683, 1990.
Lee HY, et al. "Functional analysis of Rev–responsive element of the human immunodeficiency virus type 1" Korean Biochem. J. 25: 236–243, 1992.
Yuyama N, et al. A multifunctional expression vector for an anti–HIV–1 ribozyme that produces a 5' – and 3'–trimmed trans–acting ribozyme, targeted against HIV–1 RNA, and cis–acting ribozymes that are designed to bind to and thereby sequester trans–activ, 1994.
Wong–Staal F, et al. "Viral and cellular factors that bind to the rev response element." Gen. Structure and Reg. of HIV, NY, pp. 311–322, 1991.
Sargueil B, et al. "An improved version of the hairpin ribozyme functions as a ribonucleoprotein complex." Biochem. 34: 7739–7748, Jun. 3, 1995.
Orkin SH, et al. "Report and Recommendations of the Panel to Assess the NIH Investment in Research on Gene Therapy.", Dec. 7, 1995.

*Primary Examiner*—Lynette F. Smith
*Assistant Examiner*—Amy J. Nelson
*Attorney, Agent, or Firm*—Townsend and Townsend and Crew LLP

[57] ABSTRACT

Methods and compositions for the treatment and diagnosis of infections of Rev-binding primate lentiviruses are provided. These methods and compositions utilize the ability of Rev binding nucleic acids such as the SLII sequence from the HIV-1 Rev response element (RRE) to target therapeutic agents to the same sub-cellular location as primate lentiviruses which contain RRE sequences. In particular, the invention provides trans-acting ribozymes comprising Rev-binding nucleic acids less toxic than a full-length RRE, and molecules encoding them. The use of the compositions of the invention as components of diagnostic assays, as prophylactic reagents, and in vectors is also described.

25 Claims, 7 Drawing Sheets

FIG. 5A

SEQ ID NO.: 1

SL2 Seq.
GCACTATGGGCGCAGCCTCAATGACGCTGACGGT
ACAGGCCAGACAATTATTGTCTGGTATAGTGC

FIG. 5B

SEQ ID NO.: 2

RRE Seq.
GGAGCTTTGTTCCTTGGGTTCTTGGGAGCAGCAGG
AAGCACTATGGGCGCAGCCTCAATGACGCTGACG
GTACAGGCCAGACAATTATTGTCTGGTATAGTGC
AGCAGCAGAACAATTTGCTGAGGGCTATTGAGGC
GCAACAGCATCTGTTGCAACTCACAGTCTGGGC
ATCAAGCAGCTCCAAGCAAGAATCCTAGCTGTGG
AAAGATACCTAAAGG

FIG. 6A

SEQ ID NO.: 3

SL2+U5Rz
GCACTATGGGCGCAGCCTCAATGACGCTGACGGT
ACAGGCCAGACAATTATTGTCTGGTATAGTGCgga
tccACACAACAAGAAGGCAACCAGAGAAACACA
CGTTGTGGTATATTACCTGGTacgcgt

FIG. 6B

SEQ ID NO.: 4

U5Rz+SL2
ggatccACACAACAAGAAGGCAACCAGAGAAACA
CACGTTGTGGTATATTACCTGGTacgcgtGCACTAT
GGGCGCAGCCTCAATGACGCTGACGGTACAGGCC
AGACAATTATTGTCTGGTATAGTGC

FIG. 7A

SEQ ID NO.: 5

RRE+env/rev RZ
GGAGCTTTGTTCCTTGGGTTCTTGGGAGCAGCAGG
AAGCACTATGGGCGCAGCCTCAATGACGCTGACG
GTACAGGCCAGACAATTATTGTCTGGTATAGTGC
AGCAGCAGAACAATTTGCTGAGGGCTATTGAGGC
GCAACAGCATCTGTTGCAACTCACAGTCTGGGGC
ATCAAGCAGCTCCAAGCAAGAATCCTAGCTGTGG
AAAGATACCTAAAGGggatcCTAGTTCCTAGAACC
AAACCAGAGAAACACACGTTGTGGTATATTACC
TGGTacgcgt

FIG. 7B

SEQ ID NO.: 6

SL2+env/revRz
GCACTATGGGCGCAGCCTCAATGACGCTGACGGT
ACAGGCCAGACAATTATTGTCTGGTATAGTGCgga
tcCTAGTTCCTAGAACCAAACCAGAGAAACACAC
GTTGTGGTATATTACCTGGTacgcgt

FIG. 7C

SEQ ID NO.: 7

SL2+env/revRz+SL2
GCACTATGGGCGCAGCCTCAATGACGCTGACGGT
ACAGGCCAGACAATTATTGTCTGGTATAGTGCgga
tcCTAGTTCCTAGAACCAAACCAGAGAAACACAC
GTTGTGGTATATTACCTGGTacgcgtGCACTATGGG
CGCAGCCTCAATGACGCTGACGGTACAGGCCAGA
CAATTATTGTCTGGTATAGTGC

CHIMERIC ANTIVIRAL AGENTS COMPRISING REV BINDING NUCLEIC ACIDS AND TRANS-ACTING RIBOZYMES, AND MOLECULES ENCODING THEM

CROSS REFERENCE TO RELATED APPLICATIONS

This application claims priority to provisional application U.S. Ser. No. 60/002,793, by Kraus et al., filed Aug. 25, 1995, entitled "Chimeric Antiviral Agents Which Incorporate Rev Binding Nucleic Acids" which is incorporated herein by reference in its entirety for all purposes.

STATEMENT OF GOVERNMENT SUPPORT

This invention was made with Government support under Grant No. AI36612 awarded by the National Institutes of Health. The Government has certain rights in this invention.

BACKGROUND OF THE INVENTION

The primate lentiviruses, including human immunodeficiency virus (HIV) type 1 (HIV-1), and type 2 (HIV-2) and SIV are genetically, structurally and functionally similar. HIV-1 and HIV-2 are genetically related, antigenically cross reactive, and share a common cellular receptor (CD4). See, Rosenburg and Fauci (1993) in *Fundamental Immunology, Third Edition* Paul (ed) Raven Press, Ltd., New York (Rosenburg and Fauci 1) and the references therein for an overview of HIV infection. Due to the pandemic spread of HIV-1 (and increasingly, HIV-2), an intense world-wide effort to unravel the molecular mechanisms and life cycle of these viruses is underway. It is now clear that the life cycle of these viruses provide many potential targets for inhibition by gene therapy, including cellular expression of transdominant mutant gag and env nucleic acids to interfere with virus entry, TAR (the binding site for tat, which is typically required for transactivation) decoys to inhibit transcription and trans activation, and RRE (the binding site Rev; i.e., Rev Response Element) decoys and transdominant Rev mutants to inhibit RNA processing. See, Wong-Staal et al., PCT/US94/05700; Rosenburg and Fauci (1993) in *Fundamental Imnnunology, Third Edition* Paul (ed) Raven Press, Ltd., New York and the references therein for an overview of HIV infection and the HIV life cycle, gene therapy vectors utilizing ribozymes, antisense molecules, decoy genes, transdominant genes and suicide genes, including retroviruses. See also, Yu et al., *Gene Therapy* (1994) 1:13–26. Antisense and ribozyme therapeutic agents are of increasing importance in the treatment and prevention of HIV infection.

Antisense gene therapeutic agents and ribozymes are entering clinical trials as gene therapeutic agents for the treatment of HIV infection. Ribozymes are particularly potent therapeutic agents because (i) as RNA molecules, they are not likely to induce host immunity that eliminates the transduced cells; (ii) although they resemble antisense molecules in their sequence specific recognition of target RNA, their ability to cleave the target RNA catalytically renders them more efficient than simple anti-sense molecules; and (iii) they can potentially cleave both afferent and efferent viral RNA, and therefore inhibit both preintegration and postintegration steps of the virus replication cycle. T-cell lines (Yamada et al., *Gene Therapy* (1994) 1:38–45) and primary lymphocytes (Leavitt et al., *Hum. Gene Ther.* (1994) 5:1115–1120) transduced with retroviral vectors expressing anti-HIV hairpin ribozyrnes are resistant to exogenous infection with diverse strains of HIV-1. Furthermore, macrophages derived from primary $CD34^+$ hematopoietic stem/progenitor cells were also resistant to challenge with a macrophage tropic strain of HIV-1 (Yu et al., *Virology* (1995) 206:381–386).

Because of the dramatic potential of gene therapy, constructs and methods which improve the efficacy of viral inhibitors used in gene therapy are of increasing importance. The present invention provides methods and compositions which are optionally combined with other viral inhibitors, compounds and methods to provide cells with enhanced viral resistance. The present invention also provides diagnostic reagents and methods, and kits based upon the compositions and methods of the invention.

SUMMARY OF THE INVENTION

The present invention results from the discovery that the stem loop two (SL II) sequence of the RRE is an effective viral inhibitor, and that fusion molecules which comprise the SL II sequence in conjunction with an additional viral inhibitor element are more effective than the inhibitor element alone. In particular, ribozymes which comprise the SL II sequence are catalytically active, and provide greater viral protection than similar ribozymes which lack SL II nucleic acids.

Furthermore, it is now discovered that the SL II sequence is bifunctional. As shown herein, the sequence is an effective Rev decoy, and, in addition, was shown to be sufficient to direct cellular localization of bifunctional viral inhibitors along the same cellular pathway as nucleic acids containing full-length RRE sequences (e.g., viral RNAs such as an HIV RNA). Sequences such as SL II which bind Rev are particularly potent molecular decoys, because the Rev protein multimerizes at a Rev binding site, allowing a single Rev binding nucleic acid to act as a decoy for multiple copies of the Rev protein. It is also discovered that the RRE sequence acts as a molecular decoy, and can target viral inhibitors to their target viruses. However, quite surprisingly, it is further discovered that the full-length RRE sequence is not stably expressed in cells over time, due to cytotoxicity, making it less suitable than RRE subsequences such as the SL II sequence as a viral inhibitor in general, and as a molecular decoy in particular.

Fusion molecules containing Rev binding nucleic acids such as SL II nucleic acids were shown to function as Rev decoys, while preserving the activity of the anti-viral inhibitor to which the SL II sequence was coupled (for example, ribozymes comprising the RRE and SL II sequences remain catalytically active). In addition, the activity of the anti-viral inhibitor was enhanced due to colocalization of the inhibitor and the virus, i.e., with the localization of the anti-viral inhibitor being mediated through the SL II nucleic acid portion of the molecule. Accordingly, in one class of embodiments, the present invention provides a class of inhibitors which inhibit viruses which are bound by Rev. Such viruses typically have a Rev binding nucleic acid such as an SL II sequence in their genome (e.g., HIV) e.g., as part of an RRE sequence, or a sequence with similar secondary structure. The inhibitors include nucleic acids with the SL II sequence (typically the nucleic acid is an RNA, or a nucleic acid which encodes an RNA), which act, inter alia, as molecular decoy molecules for Rev.

In addition, in many embodiments, the inhibitors of the present invention further comprise an additional moiety or moieties with a separate anti-viral activity. This additional anti-viral activity is enhanced by the addition of an SL II nucleic acid, or other Rev-binding nucleic acid which causes the inhibitor to travel along the same localization pathway as the virus, providing enhanced opportunities to interact with (and therefore inhibit) the viral nucleic acid. Although the viral inhibitor is typically a nucleic acid, other configurations are also desirable. Any viral inhibitor which interacts with viral nucleic acids benefits from the addition of the SL II nucleic acid, because the inhibitor molecule is co-localized with the viral nucleic acids. Furthermore, multiple SL II sequences can be used in combination to enhance the decoy and targeting effect of the sequences. Thus, in one preferred embodiment, the inhibitor comprises a plurality of SL II sequences (i.e., 2 or more SL II sequences). Moreover, the SL II sequence protects RNA nucleic acids from degradation by cellular nucleases by virtue of its secondary structure. Thus, in one preferred embodiment, the Rev binding sequence is attached at either the 3' or 5' terminal of an RNA (or nucleic acid encoding an RNA), or both, to protect the RNA from degradation. For example, where a viral inhibitor comprises a ribozyme, a Rev binding nucleic acid such as the SL II sequence is attached to either the 3' or 5' end of the ribozyme, or both, to inhibit degradation of the ribozyme.

Anti-sense nucleic acids can be used in the inhibitors of the present invention. In one particularly preferred class of embodiments of the invention, the inhibitor includes a ribozyme. Typically, the ribozyme cleaves a viral nucleic acid, although non-functional "ribozymes" which optionally act as anti-sense molecules are also contemplated. In one preferred embodiment, the inhibitor is a chimeric nucleic acid which includes a ribozyme such as a hairpin ribozyme, in addition to a Rev binding nucleic acid such as the SL II nucleic acid. In one preferred class of embodiments, the Rev-binding virus is an HIV virus, and the inhibitor includes a ribozyme which catalytically cleaves HIV nucleic acids.

In one class of embodiments of the invention, the invention provides viral inhibitors which comprise or encode ribozymes. In preferred embodiments of the invention, the ribozymes comprise Rev binding nucleic acids, typically at either the 5' or 3' region of the ribozyme. The ribozyme optionally comprises multiple Rev binding nucleic acids, which are at either end of the ribozyme, or both ends of the ribozyme, or in tandem at either end of the ribozyme or at both ends of the ribozyme. Typically, the viral inhibitors comprise a recombinant expression cassette, often in a gene therapy vector for transduction of cells. Typically, the gene therapy vector is designed to transduce mammalian cells with the inhibitors of the invention. Exemplar gene therapy vectors are based on retroviruses such as HIV viruses, SIV viruses, murine retroviruses, or adeno associated viruses (AAVs).

When the inhibitors of the invention are used as therapeutic agents, e.g., to provide resistance to a cell against HIV infection, the inhibitors are typically placed into a gene therapy vector such as a retroviral (e.g., HIV, SIV or MuLV) or an AAV-derived vector for transduction of a target cell upon which resistance to viral infection or replication is to be conferred. Such vectors can be used to transduce cells in vitro, ex vivo, or in vivo. Thus, the present invention provides cells which express the inhibitors of the invention in vitro, or in vivo. Exemplar cells include cells which express the CD4 receptor on their cell surface (e.g., when the gene therapy vector recognizes CD4+ cells, e.g., where the vector is encapsulated in an HIV capsid or envelope), such as monocytes, lymphocytes and macrophage. The cells exist as individual cells, e.g., in a cell culture, or as part of a tissue, e.g., in tissue cultures or organs, or in whole organisms, such as mammals (including primates such as humans and macaques).

The inhibitors and nucleic acids encoding the inhibitors of the invention can be incorporated into many other types of cells as well. For instance, where the inhibitor is an RNA molecule, the RNA or the corresponding nucleic acid can be cloned into a variety of recombinant cells, including prokaryotes and eukaryotes. Where non-retroviral gene therapy vectors are used, the inhibitors are present in cell types transduced by the vector. For instance, AAV vectors infect most known eukaryotic cells. Thus, AAV vectors are a preferred gene therapy vector for the incorporation of the inhibitors of the invention into cells, particularly where the cells are present in a whole animal (e.g., a mammal). Organ specific gene therapy vectors are also known. For instance, hepatocyte virus vectors target the liver, due to the specificity of hepatocyte viruses for the liver. As already described, HIV-based vectors target CD4+ cells in vivo.

The methods of the present invention provide means for inhibiting the growth, replication and expression of Rev-binding viruses in cells. These methods operate by transducing cells with an inhibitor of the invention. In one preferred class of embodiments, the methods of the invention inhibit a Rev-binding virus in a mammal. In a most preferred embodiment, the methods of the invention are used to inhibit an HIV virus in a human.

Most commonly in the methods of the invention, the inhibitor is introduced into a target cell using a gene therapy vector, such as a retroviral vector, or an AAV based vector. The cells are optionally in vitro cells, such as cultured cells from a blood bank, ex vivo cells, such as CD4+ cells isolated from a mammal, or in vivo cells, i.e., where the gene therapy vector transduces cells in a whole organism, such as a mammal (including a human). Such gene therapy vectors include vectors with the HIV packaging site (e.g., HIV-1 ψ) and the AAV packaging site in the AAV inverted terminal repeat (ITR).

In one embodiment, the present invention provides methods for the detection of Rev-binding viral infections. In these methods, cells are monitored for the presence of Rev in an in vitro binding assay, using an inhibitor of the invention which includes an SL II nucleic acid. For instance, a gel mobility-shift assay using a radio-labeled SL II nucleic acid can be used to detect Rev in a cell extract, providing an indication that the cells used to make the extract are infected with a virus (e.g., HIV) which encodes Rev. In another diagnostic embodiment, cells suspected of being infected with a Rev-binding virus are transduced with an inhibitor of the invention. Increased survival compared to an untransduced control is diagnostic for the presence of a Rev-binding protein.

The compositions of the invention further provide a prophylactic utility. The safety of handling and maintaining cell cultures is enhanced by incorporating the inhibitors of the invention into the cells of the cell culture, because the cells are rendered resistant to pathogenic viruses such as HIV. Because the cells are less likely to be infected with a pathogenic virus, workers handling the cells are less likely to contract the virus from the cell culture.

The compositions and methods of the invention can be incorporated into kits for the treatment and diagnosis of Rev-binding viral infections. Typically, these kits include a container and a nucleic acid of the invention. The kits optionally include additional components such as instructional materials, reagents for cellular transfection and control cells.

and stem-loop II sequences (SL II) of the HIV-1 RRE. The fusion RNA is driven by an internal human tRNA$^{val}$ promoter. Panels (B) and (C) show the inhibition of p24 antigen expression after challenge with HIV-1 SF2 at a M.O.I. of 0.01. (panel B) MOY-1 cells (expressing anti-Rev ribozyme), MSLOY-1 cells (expressing anti-Rev ribozyme linked to SL II), and parental Molt-4/8 cells were infected with SF2 (panel C) MMJT (expressing anti-U5 ribozyme), MdMJT (expressing disabled anti-U5 ribozyme), MSLMJT (expressing anti-U5 ribozyme linked to SL II), and Molt-4/8 cells were infected with SF2. Culture supernatants were used for measurement of HIV-1 p24 antigen. □: Molt-4/8; Δ: MOY-1; ○: MSLOY-1; ▲: MMJT; ●: MSLMJT; ■: MdMJT.

FIGS. 2A–2D shows ribozyme expression levels in stable cell lines. Total cellular RNA from MMJT(A), MdMJT(B), MSLMJT(C), and MSLdMJT(D) cultured for 25 weeks after initial transfection was subjected to RT-PCR amplification in the presence of different amounts of competitor RNA. Ten μl of each PCR product was loaded onto a 5% low melting agarose gel and stained with ethidium bromide. Video images of the gel were inverted with Adobe Photoshop v3.0. The number of copies of competitor RNA added to each PCR reaction was as follows: Lanes 1: $10^8$; 2: $10^7$; 3: $10^6$; 4: $10^5$; 5: 0.

Figure 3A:
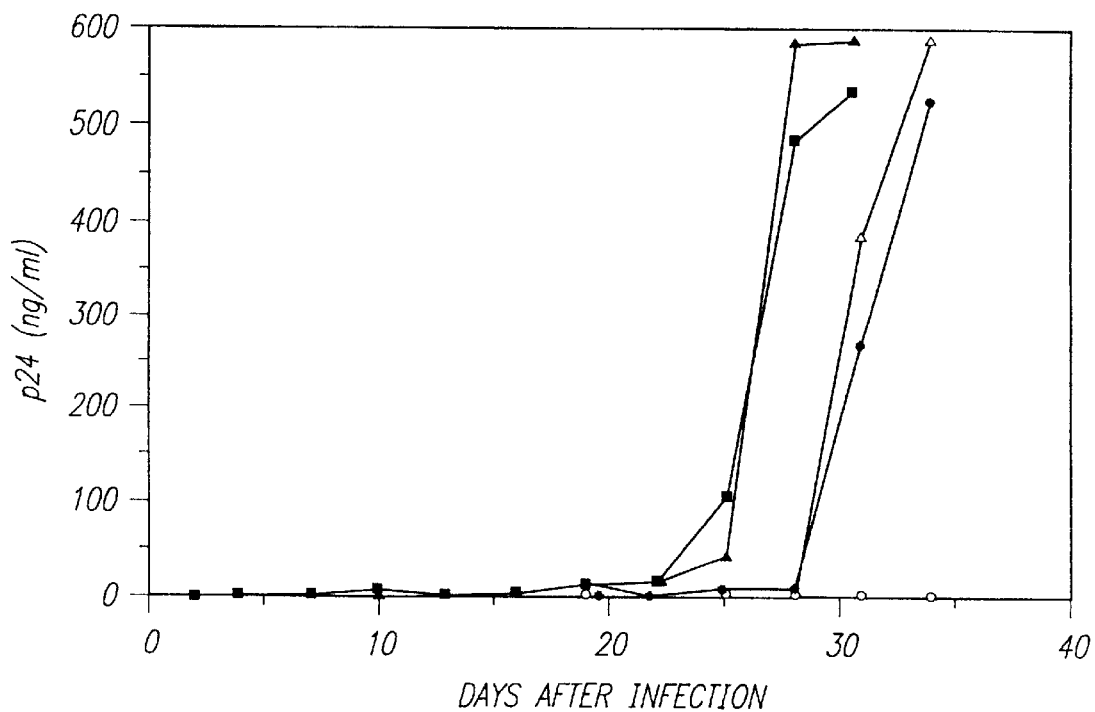
Figure 3B:
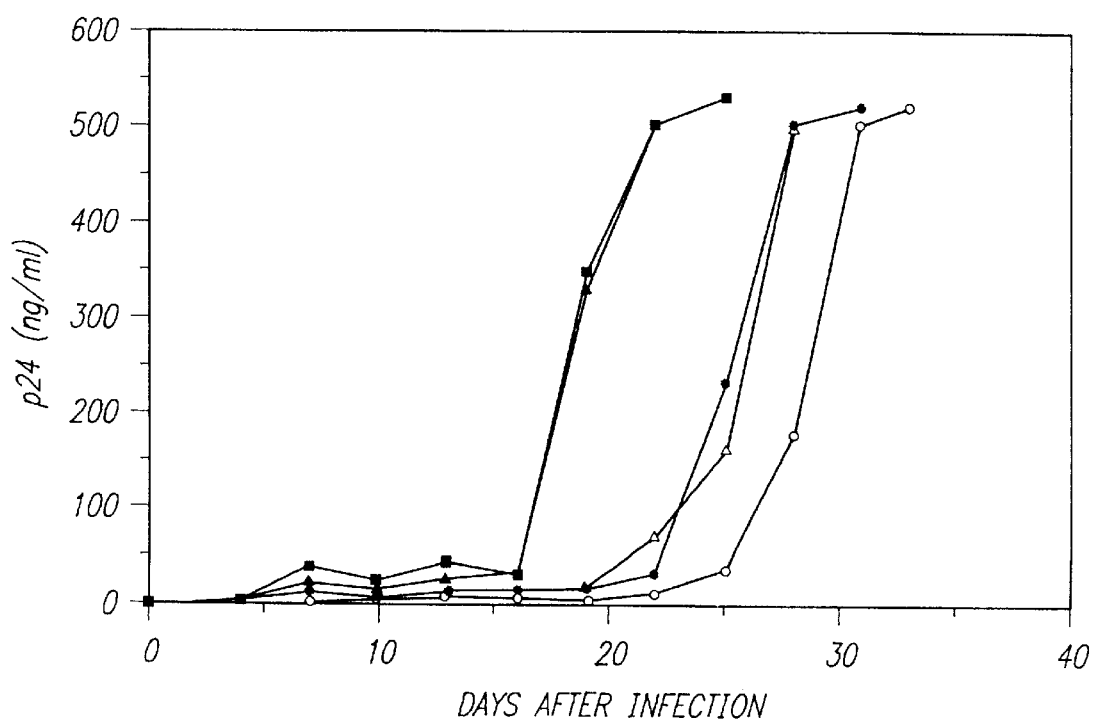

FIGS. 3A–3B show the inhibition of p24 expression in cell-cell transmission of HIV-1. $10^5$ MLNL6 (■), MMJT(Δ), MdMJT(▲), MSLMJT(○),or MSLdMJT(●) cells were suspended in 1 ml of 10% FCS supplemented RPMI 1640 with (A). 100 (1000:1 uninfected to infected cells) or (B). 1000 cells (100:1) of Jurkat cells chronically infected with HXB2. Four days after infection, the cells were split to adjust the cell concentraton to $2\times10^5$ cells/inl, and further split 1 to 5 every 3 days thereafter. The culture supernatants were used for measurement of p24 antigen level.

Figure 4A:
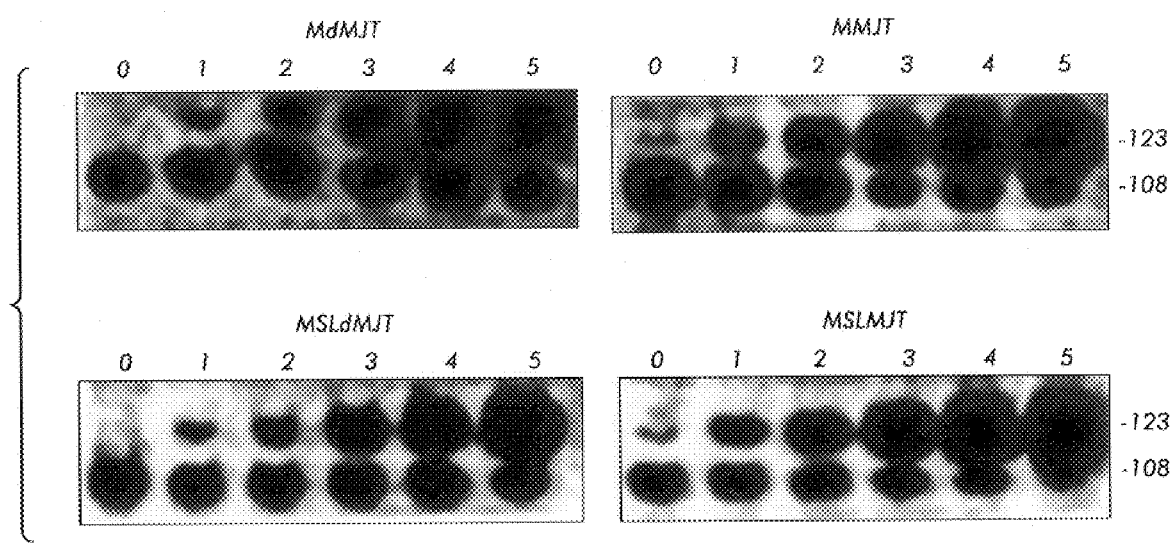
Figure 4B:
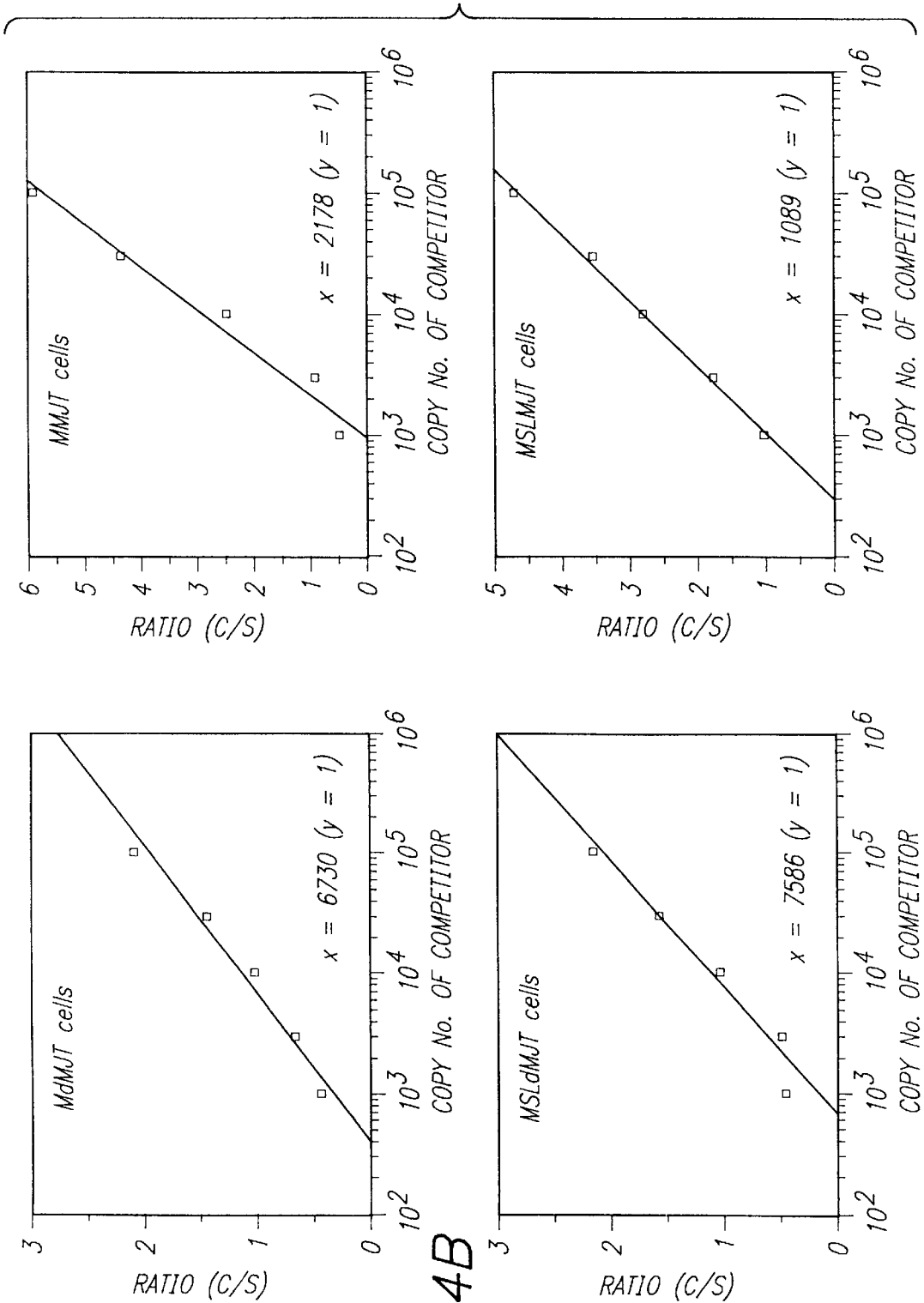

FIGS. 4A–4B show reduction of proviral DNA burden during a first round infection. After infection of MMJT, MdMJT, MSLMJT, or MSLdMJT cells with HIV-1 HXB2 for 7 hrs, cell lysates were prepared from the infected cells to provide template DNAs for quantitative competitive PCR. The PCR was carried out using a $^{32}$P-end-labeled-SK29/SK30 primer pair derived from the HIV-1 LTR in the presence of different concentrations of competitor DNA. The expected sizes of the amplified products were 105 bp and 123 bp, respectively, for the test and competitor DNA. After PCR, 3 μl each of the PCR products was loaded on 8% polyacrylamide gel, electrophoresed for 16 hours and autoradiographed (panel A). Images of the gel was scanned by Twain Scan Duo 600 (Mustek) and analyzed using NIH image v.1.54 by THE Macintosh computer (panel B). Ratio C/S; ratio of the signal intensity of the products of the competitor DNA and sample DNA.

FIGS. 5A–5B represent example sequences for SL II, and the RRE sequence (SEQ ID NO:1 and SEQ ID NO:2, respectively).

FIGS. 6A–6B represent ribozymes which comprise Rev binding nucleic acids. Panel A is a representation of a ribozyme which comprises an SL II nucleic acid, and which cleaves the U5 region of HIV-1. Panel B is a similar ribozyme with the SL II sequence at the 3' terminus instead of the 5' terminus as shown in panel A. Lower case nucleic acids represent restriction sites. Panels A and B represent SEQ ID NO:3 and SEQ ID NO:4, respectively.

FIGS. 7A–7C represent ribozymes which comprise Rev binding nucleic acids. Panel A represents a ribozyme which cleaves HIV-1 nucleic acids in the env/rev region, with a 5' Rev binding nucleic acid corresponding to the HIV-1 RRE. Panel B represents a similar env/rev ribozyme, with 5' SL II nucleic acid. Panel C represents a similar env/rev ribozyme with 5' and 3' SL II nucleic acids. Panels A, B, and C represent SEQ ID NO:5, SEQ ID NO:6 and SEQ ID NO:7, respectively.

DEFINITIONS

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A "Rev-binding virus" is a virus or derivative thereof, which comprises nucleic acid sequence elements necessary and sufficient to direct binding of a Rev protein. Most typically, the virus will be a primate lentivirus such as an HIV virus which comprises a Rev response element (RRE), or a subsequence thereof, such as the SL II sequence from HIV-1. Many allelic and strain variants of the Rev protein and the RRE are known for primate lentiviruses, particularly HIV viruses. In addition, the SL II sequence, optionally in conjunction with other RRE sequences can easily be engineered into any virus, viral vector or nucleic acid encoded by either the virus or vector using standard recombinant techniques described herein. In this way, any virus or vector can be converted into a Rev-binding virus.

A Rev binding sequence is a nucleic acid which specifically binds to Rev in vitro or in vivo (typically an RNA), or to a nucleic acid which encodes a nucleic acid which binds to Rev in vitro or in vivo (i.e., an RNA or a DNA). An Example of a Rev binding nucleic acid is the RNA corresponding to an SL II nucleic acid, described herein. The RRE also binds to Rev. Several papers describe in vitro binding assays for monitoring Rev binding, including Wong-Staal et al. (1991) Viral And Cellular Factors that Bind to the Rev Response Element in *Genetic Structure and Regulation of HIV* (Haseltine and Wong-Staal eds.; part of the Harvard AIDS Institute Series on Gene Regulation of Human Retroviruses, Volume 1), pages 311–322 and the references cited therein, which describe gel mobility-shift assays and footprinting assays for the detection of Rev in biological samples, including human blood.

An SL II nucleic acid is a nucleic acid which comprises the stem loop two region (SL II) of the HIV RRE, or a conservatively modified variation thereof. SEQ ID NO 1 provides an example SL II sequence.

An "inhibitor" or "viral inhibitor" is most typically a nucleic acid which encodes an active anti-viral agent, or is itself an anti-viral agent. Thus, in one class of embodiments, the inhibitor is a "direct inhibitor," i.e., the inhibitor acts directly on a viral component to inhibit the infection, replication, integration or growth of the virus in the cell. For instance, in one particularly preferred embodiment, the inhibitor comprises a trans-active ribozyme which cleaves a Rev-binding virus nucleic acid (e.g., an HIV transcript). In this configuration, the inhibitor is typically an RNA molecule with catalytic nuclease activity. In another class of embodiments, the inhibitor is an "indirect inhibitor," i.e., the inhibitor encodes the direct inhibitor. For instance, in one preferred embodiment, the inhibitor is part of a gene therapy vector, which, when expressed, produces an anti-viral RNA which includes an SL II molecular decoy. For example, in one preferred embodiment, the inhibitor is a transcription cassette which is encoded by a gene therapy vector which is used to transfect a cell, where the transcription cassette expresses a nucleic acid which encodes an SL II nucleic acid, and, optionally, a ribozyme or antisense molecule which inhibits the ability of a rev-binding virus such as HIV-1 to replicate in the cell. An inhibitor "encodes" a direct inhibitor such as an active ribozyme, RNA molecular decoy, or anti-sense RNA if it contains either the sense or anti-sense coding or complementary nucleic acid which corresponds to the direct inhibitor. By convention, direct inhibitor RNAs such as ribozymes are typically listed as their corresponding DNA sequences. For instance, in SEQ ID NOs:1–7 herein, sequences are listed 5' to 3' as the DNA which corresponds directly to the encoded RNA. This is done to simplify visualization of the corresponding active RNA, which is equivalent to the given sequence with the T residues replaced by U residues.

Although the inhibitor is typically an RNA, or a nucleic acid which encodes the RNA (i.e., DNA or RNA), other configurations are also possible. For instance, in one embodiment, the inhibitor includes protein or other elements with antiviral activity. For example, in one embodiment, the inhibitor comprises an SL II nucleic acid and a bound Rev protein (e.g., an endogenous protein from the cell, or a Rev protein from an invading virus). In one embodiment, the inhibitor optionally includes nucleic acids which encode separate protein binding sites such as the TAR site for Tat binding, and the bound protein.

"Viral inhibition" refers to the ability of a construct to inhibit the infection, growth, integration, or replication of a virus in a cell. Inhibition is typically measured by monitoring changes in a cell's viral load (i.e., the number of viruses and/or viral proteins or nucleic acids present in the cell, cell culture, or organism) or by monitoring resistance by a call, cell culture, or organism to infection.

A "targeted anti-HIV chimeric nucleic acid" refers either to a nucleic acid which encodes an SL II nucleic acid and an anti- Rev-binding virus agent (such as a ribozyme or an anti-sense molecule which inhibits the Rev-binding virus), or to the encoded nucleic acid. Thus, in one embodiment, the targeted anti-HIV chimeric nucleic acid is part of a gene therapy vector which encodes an SL II nucleic acid and a Rev-binding viral element. In a second embodiment, the targeted anti-HIV chimeric nucleic acid is a nucleic acid (typically an RNA) which includes an SL II sequence and an anti-Rev-binding viral agent (e.g., ribozyme or anti-sense) sequence.

Ribozymes are typically either "cis-ribozymes" or trans-ribozymes. Cis ribozymes cleave the nucleic acid which they are part of, whereas trans-ribozymes catalytically cleave nucleic acids which they are not covalently linked to. A ribozyme optionally has both cis- and trans- activity, and in some embodiments, a cis-ribozyme is converted into a trans ribozyme after a cis cleavage event.

The term "identical" in the context of two nucleic acids refers to the nucleotide residues in the two sequences which are the same when aligned for maximum correspondence.

Methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipinan (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual adjustment of the sequences.

The terms "isolated" or "biologically pure" refer to material which is substantially or essentially free from components which normally accompany it as found in its native state. The isolated nucleic acids of this invention do not contain materials normally associated with their in situ environment, in particular, nuclear, cytosolic or membrane associated proteins or nucleic acids other than those nucleic acids which are indicated.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence implicitly provides the complementary sequence thereof, as well as the sequence explicitly indicated.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means.

A "recombinant expression cassette" or simply an "expression cassette" is a nucleic acid construct, generated recombinantly or synthetically, with nucleic acid elements which permit transcription of a particular nucleic acid in a cell. The recombinant expression cassette can be part of a plasmid, virus, or nucleic acid fragment. Typically, the recombinant expression cassette includes a nucleic acid to be transcribed, and a promoter. In some embodiments, the expression cassette also includes, e.g., an origin of replication, and/or chromosome integration elements (e.g., an AAV ITR, or retroviral LTR).

The term "subsequence" in the context of a particular nucleic acid sequence refers to a region of the nucleic acid equal to or smaller than the specified nucleic acid.

DETAILED DISCUSSION OF THE INVENTION AND DESCRIPTION OF PREFERRED EMBODIMENTS

The molecular receptor for HIV is the surface glycoprotein CD4 found mainly on a subset of T cells, monocytes, macrophage and some brain cells. HIV has a lipid envelope with viral antigens that bind the CD4 receptor, causing fusion of the viral membrane and the target cell membrane and release of the HIV capsid into the cytosol. HIV causes cell death of these immune cells, thereby disabling the immune system and eventually causing death of the patient due to complications associated with a disabled immune system. HIV infection also spreads directly from cell to cell, without an intermediate viral stage. During cell-cell transfer of HIV, a large amount of viral glycoprotein is expressed on the surface of an infected cell, which binds CD4 receptors on uninfected cells, causing cellular fusion. This typically produces an abnormal multinucleate syncytial cell in which HIV is replicated and normal cell functions are suppressed.

Recent studies of the dynamics of HIV replication in patients under antiviral therapy have reaffirmed the central role of the virus in disease progression, and provided a strong rationale for the development of effective, long term antiviral therapy (Coffin, J. M. *Science* (1995) 267:483–489; Ho et al., *Nature* (1995) 373:123–6; Wei et al., *Nature* (1995) 373:117–22). One interesting parameter from these studies is the extremely short life span of an HIV-1 infected $CD4^+$ lymphocyte (half life=1–2 days), contrasting data from other studies which gave an estimated lifespan of months to years for uninfected lymphocytes (Bordignon et al., *Hum Gene Ther.* (1993) 4:513–20). These observations are relevant for antiviral gene therapy, because an "intracellularly immunized" cell resistant to viral infection, or which suppresses viral replication will be strongly selected for in vivo.

In previous studies, the efficacy of several anti-HIV-1 hairpin ribozymes in inhibiting virus replication in human T cell lines was demonstrated. See, Wong-Staal et al., PCT/US94/05700; Yamada et al., *Virology* (1994) 205:121–126; Yamada et al., *Gene Therapy* (1994) 1:38–45; Yu et al., *Proc Natl. Acad. Sci. USA* (1993) 90:6340–6344; Yu et al., *Virology* (1995) 206:381–386 and Yu et al. (1993) PNAS 90: 6340–6344. With an anti-U5 ribozyme which targets a highly conserved region of the HIV-1 genome, it was shown that intracellular immunization of primary lymphocytes or viral hematopoietic progenitor cells could lead to resistance to both lymphotropic and macrophage tropic HIV-1 strains (Leavitt et al., *Humn. Gene Ther.* (1994) 5:1115–1120; Yu et al., *Proc. Natl. Acad. Sci. USA* (1995) 92:699–703).

To increase antiviral potency of anti-viral inhibitors such as ribozyme vectors, as well as to reduce the chance of viral resistance, we explored the possibility of adding other antiviral agents to the ribozyme constructs.

Rev, an early gene product of HIV, controls expression of the HIV-1 structural genes through binding to a Rev Response Element (RRE) present in unspliced or partially spliced viral transcripts. Rev facilitates the nuclear export and utilization of such transcripts in the cytoplasm (Feinberg et al., *Cell* (1986) 46:807–817; Malim et al., *Nature* (1989) 338:254–257). We hypothesized that linking the RRE sequence to a ribozyme would improve efficacy of the ribozyme because such a molecule would be bifunctional (e.g., by providing a nuclease+Rev decoy effect). In addition, we hypothesized that ribozyme activity would also be facilitated by linking the ribozyme to the RRE, because the RRE would stabilize the ribozyme molecule by inhibiting degradation of the ribozyme. Furthermore, as described herein, we found that binding of Rev to the RRE-ribozyme fusion molecule traffics the fusion molecule along the same nuclear-cytoplasmic pathway as HIV mRNA (which is Rev dependent), thereby increasing the opportunity for interaction between the ribozyme and the HIV substrate. Finally, we found that binding of Rev to the ribozyme-substrate complex increases the turnover of the ribozyme, resulting in increased catalytic activity.

The HIV-1 RRE is 234 nt in length, predicted to form a central stem and five stem-loop structures (Feinberg et al., *Cell* (1986) 46:807–817). The entire full-length RRE sequence was inserted into a ribozyme expression cassette. For the first time, such a combination of the RRE and ribozyme was shown to produce a functional ribozyme, and the construct displayed strong viral inhibition. Surprisingly, however, although cell lines expressing such fusion RNAs demonstrated strong virus inhibition, expression of the fusion RNA (RRE+ribozyme) was turned off at week 15 after transfection. While not being bound to a particular theory, it is hypothesized that interaction between the RRE and one or more mammalian cellular proteins (which is known to occur, see, Vaishnav et al., *New Biol.* (1991) 3:142–150) induces cellular toxicity and provides negative selection for cells expressing the fusion RNA.

To overcome the unexpected property of cytotoxicity by RRE, a minimal sequence comprising the second stem loop of RRE (SL II) was cloned and tested in the ribozyme constructs. An SL II-anti-U5 ribozyme fusion RNA was shown to be persistently expressed in stable cell lines for over 25 weeks. It was also found to be more effective in virus inhibition than the ribozyme alone, or the SL II nucleic acid linked with a disabled ribozyme (See also, FIG. 3).

The decoy effect of the fusion RNA was demonstrated by HIV-1 SF2 infection of a stable cell line, MSLOY-1, expressing the SL II sequence linked to an anti-Rev ribozyme. HIV-1 SF2 is refractory to inhibition by the anti-Rev ribozyme because of a substitution at the G residue at the site of cleavage (FIG. 1B) (see also, Yamada et al., *Virology* (1994) 205:121–126). Therefore, the observed inhibitory effect of the fusion RNA is due to the SL II sequence acting as a decoy.

Also demonstrated herein is the ribozyme activity of the fusion RNA by showing a reduction of proviral DNA burden in a first round infection (see, e.g., FIG. 4). Additionally, the fusion RNA exerted a two fold greater reduction in viral DNA synthesis than the ribozyme alone. Bertrand, et al., *Embo J.* (1994) 13:2904–12 reported that adding the nucleocapsid protein of HIV-1, or the heterogeneous ribonucleoprotein A1 to the cleavage reaction of hammerhead ribozymes was able to increase binding, specificity, and turnover of the ribozymes in vitro without inhibiting cleavage, depending on the length of the ribozyme-substrate duplexed region. The time-regulated nuclear export of Rev is correlated with protein expression from RRE-containing mRNAs, and distribution of Rev reflects its interaction with RRE-containing RNA and migration of the bound transcript from the nucleolus across a solid phase of nucleus and nuclear membrane to the cytoplasm through a specific export pathway (Luznik et al., *AIDS Res. Hum. Retrovirus* (1995) 11:795–804). SL II fusion RNA (like other Rev-binding nucleic acid fusion RNAs) traffics through the same cellular compartments as HIV mRNA caused by the binding of Rev, thereby increasing the efficiency of the ribozyme by increasing the opportunity for interaction between the ribozyme and the viral nucleic acid.

Viral Inhibitors

Viral inhibitors of the invention take several forms. Typically, the viral inhibitor is a nucleic acid which has direct anti-viral activity, such as a molecular decoy, antisense RNA or ribozyme, or indirect anti-viral activity, i.e., where the inhibitor encodes a direct anti-viral activity (e.g., where the inhibitor encodes a ribozyme RNA, for example in conjunction with an SL II sequence). The inhibitors of the invention typically include an SL II nucleic acid, either in its active (i.e., RNA) molecular decoy form, or in its encoded form (i.e., in an RNA or DNA vector which encodes the active form). Thus, techniques applicable to the construction and maintenance of nucleic acids apply to the nucleic acid inhibitors of the present invention.

In preferred embodiments, the inhibitors of the invention include ribozymes, such as hairpin ribozymes (see, Wong-Staal et al. WO 94/26877 and PCT/US94/05700 and the references therein; see also, Yu et al. (1993) PNAS 90: 6340–6344; and Yu et al. (1995) Virology 206: 381–386), hammerhead ribozymes (see, Dropulic et al. (1992) Journal of Virology, 66(3):1432–1441), and RNAse P (see, Castanotto et al. (1994) Advances in Pharmacology Academic Press 25: 289–317). These ribozymes are constructed to target a portion of the Rev-binding virus' genome or nucleic acid encoded by the genome. Preferred target sites in HIV-1 include the U5 region, and the polymerase gene.

Antiviral Agents: antisense nucleic acids, ribozymes, decoy nucleic acids and trans-dominant proteins Viral inhibitors optionally comprise antiviral agents. Antiviral agents are known in the art. The literature describes such genes and their use. See, for example, Yu et al., *Gene Therapy*, 1:13 (1994); Herskowitz, *Nature*, 329:212 (1987) and Baltimore, *Nature*, 335:395 (1988). Anti-viral agents which are optionally incorporated into the viral inhibitors of the invention include anti-sense genes, ribozymes, decoy genes, and transdominant proteins.

An antisense nucleic acid is a nucleic acid that, upon expression, hybridizes to a particular RNA molecule, to a transcriptional promoter or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to viral gene transcripts. Two target sequences for antisense molecules are the first and second exons of the HIV genes tat and rev. Chatterjee and Wong, supra, and Marcus-Sekura (*Analytical Biochemistry* (1988) 172, 289–285) describe the use of anti-sense genes which block or modify gene expression.

A ribozyme is a catalytic RNA molecule that cleaves other RNA molecules having particular nucleic acid sequences. General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25: 289–317 provides an overview of ribozymes in general, including group I ribozymes, hammerhead ribozymes, hairpin ribozymes, RNAse P, and axhead ribozymes. Ribozymes useful in this invention include those that cleave viral transcripts, particularly HIV gene transcripts. Ojwang et al., *Proc. Nat'l. Acad. Sci., U.S.A.*, 89:10802–06 (1992); Wong-Staal et al. (PCT/US94/05700); Ojwang et al. (1993) *Proc Natl Acad Sci USA* 90:6340–6344; Yamada et al. (1994) *Human Gene Therapy* 1:39–45, Leavitt et al. (1995) *Proc Natl Acad Sci USA* 92:699–703, Leavitt et al. (1994) *Human Gene Therapy* 5:1151–1120; Yamada et al. (1994) *Virology* 205:121–126, and Dropulic et al. (1992) *Journal of Virology* 66(3):1432–1441 provide examples of HIV-1 specific hairpin and hammerhead ribozymes.

Briefly, two types of ribozyines that are particularly useful in this invention include the hairpin ribozyme and the hammerhead ribozyme. The hammerhead ribozyme (see, Rossie et al. (1991) *Pharmac. Ther.* 50:245–254; Forster and Symons (1987) *Cell* 48:211–220; Haseloff and Gerlach (1988) *Nature* 328:596–600; Walbot and Bruening (1988) *Nature* 334:196; Haseloff and Gerlach (1988) *Nature* 334:585; and Dropulic et al and Castanotto et al., and the references cited therein, supra) and the hairpin ribozyme (see, e.g., Hampel et al. (1990) *Nucl. Acids Res.* 18:299–304; Hempel et al., (1990) European Patent Publication No. 0 360 257; U.S. Pat. No. 5,254,678, issued Oct. 19, 1993; Wong-Staal et al., PCT/US94/05700; Ojwang et al. (1993) *Proc Natl Acad Sci USA* 90:6340–6344; Yamada et al. (1994) *Human Gene Therapy* 1:39–45, Leavitt et al. (1995) *Proc Natl Acad Sci USA* 92:699–703, Leavitt et al. (1994) *Human Gene Therapy* 5:1151–1120; and Yamada et al. (1994) *Virology* 205:121–126) are catalytic molecules having antisense and endoribonucleotidase activity. Intracellular expression of hammerhead ribozymes and hairpin ribozymes directed against HIV RNA has been shown to confer significant resistance to HIV infection.

The typical sequence requirement for cleavage by a hairpin ribozyme is an RNA sequence consisting of NNNG/CN*GUCNNNNNNNN (SEQ ID NO:8)(where N*G is the cleavage site, and where N is any of G, U, C, or A). The sequence requirement at the cleavage site for the hammerhead ribozyme is an RNA sequence consisting of NUX (where N is any of G, U, C, or A and X represents C, U or A). Accordingly, the same target within the hairpin leader sequence, GUC, is targetable by the hammerhead ribozyme. The additional nucleotides of the hammerhead ribozyme or hairpin ribozyme which mediate sequence specificity, are determined by the common target flanking nucleotides and the hammerhead and hairpin consensus sequences.

Altman (1995) *Biotechnology* 13: 327–329 and the references therein describe the use of RNAse P as a therapeutic agent directed against flu virus. Similar therapeutic approaches can be used against Rev binding viruses such as HIV by incorporating RNAse P into the inhibitors of the invention.

The ribozymes of this invention and DNA encoding the ribozymes, can be chemically synthesized as described in more detail below using methods known in the art, or prepared from a DNA molecule (that upon transcription, yields an RNA molecule) operably linked to an appropriate promoter.

A decoy nucleic acid is a nucleic acid having a sequence recognized by a regulatory nucleic acid binding protein (i.e., a transcription factor, cell trafficking factor, etc.). Upon expression, the transcription factor binds to the decoy nucleic acid, rather than to its natural target in the genome. Useful decoy nucleic acid sequences include any sequence to which a viral transcription factor binds. For instance, the TAR sequence, to which the tat protein binds, and the HIV RRE sequence (in particular the SL II sequence), to which the rev protein binds are suitable sequences to use as decoy nucleic acids.

A transdominant protein is a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. In particular, rev can be made transdominant by eliminating the leucine-rich domain close to the C terminus which is essential for proper normal regulation of transcription. Tat transdominant proteins can be generated by mutations in the RNA binding/nuclear localization domain. Transdominant proteins can be encoded by the inhibitors of the invention, for instance, in an expression cassette which also includes, e.g., the SL II molecular decoy in conjunction with a ribozyme.

Examples of antisense molecules, ribozymes and decoy nucleic acids and their use can be found in Weintraub, *Sci. Am.*, 262:40–46 (January 1990); Marcus-Sekura, *Anal. Biochem.*, 172:289–95 (1988); and Hasselhoff et al., *Nature*, 334:585–591 (1988), incorporated herein by reference.

Making Viral Inhibitors

The present invention provides a variety of viral inhibitors as described supra. Typically, these viral inhibitors are nucleic acids such as the SL II sequence, ribozymes against HIV or anti-sense sequences, or the corresponding nucleic acids which encode such nucleic acids.

Given the general strategy for making viral inhibitor nucleic acids of the present invention, one of skill can construct a variety of clones containing viral inhibitors and derivative clones. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosysteins (Foster City, Calif.), as well as many other commercial sources known to one of skill.

The nucleic acid compositions of this invention, whether RNA, cDNA, genomic DNA, or a hybrid of the various combinations, are isolated from natural sources or synthesized in vitro. The nucleic acids claimed are present in transformed or transfected whole cells, in transformed or transfected cell lysates, or in a partially purified or substantially pure form.

In vitro amplification techniques suitable for amplifying provirus sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as probes, e.g., in in vitro amplification methods, for use as gene probes, or as inhibitor components are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook, Innis, Ausbel, Berger, Needham VanDevanter and Mullis (all supra).

One of skill can select a desired inhibitor nucleic acid of the invention based upon the sequences and strategies provided herein, and upon knowledge in the art regarding primate lentiviruses generally. The life-cycle, genomic organization, developmental regulation and associated molecular biology of lentiviruses such as HIV and SIV viruses have been the focus of over a decade of intense research. The specific effects of many mutations in the primate lentiviral genome are known, and the interaction of many of the components of the viruses at a molecular level are known.

Polypeptides of the invention can be synthetically prepared in a wide variety of well-known ways. For instance polypeptides of relatively short size, can be synthesized in solution or on a solid support in accordance with conventional techniques. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synthesis*, 2d. ed., Pierce Chemical Co. More typically, polypeptides are produced by recombinant expression of a nucleic acid encoding the polypeptide and purification, using standard techniques.

Rev Binding Nucleic Acids: The SL II sequence and the RRE

Rev binding nucleic acids are defined functionally to consist of nucleic acids which bind to Rev, or which encode nucleic acids which bind to Rev. A variety of sequences which bind Rev are known. Different Rev proteins are known for different viruses (e.g., Rev-1 from HIV-1, and Rev-2 from HIV-2, and the sequence requirements for each are similar, though not identical. For instance, even though the HIV-2 Rev protein cannot substitute for the HIV-1 Rev protein by transcomplementation, both HIV-1 and HIV-2 forms of the Rev protein (Rev-1 and Rev-2) bind to the HIV-1 RRE, with roughly equivalent sequence specificity for the HIV-1 stem loop-2 region (See, Garrett and Cullen (1992) *J. Virol.* 66(7): 4288–4294).

The SL II region from HIV-1 (comprising 66 nt from the HIV-1 RRE) is a suitable Rev-binding nucleic acid of the invention (See, SEQ ID NO:1). The HIV-1 RRE (See, SEQ ID NO:2; 234 nt) also binds Rev, and can be used in the inhibitors of the invention. However, the complete RRE is not preferred in applications where the inhibitor is expressed in a cell to produce viral inhibition, because expression of nucleic acids containing the complete HIV-1 RRE is down-regulated in cells, due to apparent cytotoxicity. Additional Rev binding proteins are constructed which comprise the SL II sequence, but which lack the full-length RRE sequence by cloning and expressing RRE sub-sequences which contain the SL II sequence. Indeed, the complete SL II sequence is not necessary for Rev binding, and sub-sequences of SL II are optionally used in the inhibitors of the invention. Typically, the SL II subsequences which bind Rev comprises at least 10 consecutive nucleotides from SL II, more typically at least about 20 consecutive nucleoctides from SL II, preferably 30 consecutive nucleotides from SL II, still more preferably 40 consecutive nucleotides from SL II, ideally at least about 40 consecutive nucleotides from SL II, and most preferably at least about 50 consecutive nucelotides from SL II. However, larger Rev binding nucleic acids which comprise the SL II sequence are typically preferred, particularly when the inhibitors of the invention comprise or encode ribozymes or other RNA molecules. This is because the secondary structure of the Rev binding site (e.g., the stem loop of SL II) protect other RNA components of the inhibitor from degradation by cellular RNAse enzymes.

Accordingly, in preferred embodiments, a Rev binding nucleic acid comprises an SL II nucleic acid. One of skill can easily add flanking sequences from the RRE (or other heterologous nucleic acid) to the SL II sequence by synthesizing and subcloning appropriate nucleic acids. The sequences within the RRE which result in inhibition of expression of the inhibitors containing the construct can be determined by standard deletion analysis of the RRE. Briefly, RRE subsequences to be tested for activity as shown in the examples below are cloned into the same vectors which were shown herein to provide inhibition of Rev binding viruses. The subsequences containing SL II sequence plus additional flanking sequence from the RRE are combined with a ribozyme as described herein, and inhibitory effect is monitored as determined herein. Sequences which stably provide an inhibitory effect for more than 15 weeks are suitable Rev binding sites. At a given point between the 66 nt of the full-length SL II and the full length 234 nt RRE, inhibition of the expression of the inhibitor (i.e., due to cytotoxicity) is observed. If deletions (i.e., SL II sequences+RRE flanking sequences) are made, for instance, every 10 nt, then each 10 nt subsequence between the SL II sequence and the full-length RRE can easily be monitored for resulting cytotoxicity of the inhibitor. Particular regions within the RRE which cause cytotoxicity are omitted from preferred embodiments.

The SL II Rev binding site is typical of Rev binding sites, in that Rev primarily recognizes the secondary structure of the nucleic acid (i.e., the stem-loop structure). Modifications are made to the sequence to result in functionally similar (i.e., Rev-binding) sequences by modifying the sequence such that the secondary structure of the nucleic acid is retained. This is done by altering corresponding nucleotides in the structure to yield equivalent nucleic acid hybridization in the secondary structure of the nucleic acid. For instance, in a region of the secondary structure where a C binds to a G, the two nucleotides can be reversed to yield the same overall secondary structure of the molecule. The ability of the resulting sequence to bind Rev is monitored in standard gel mobility-shift assays as described herein. Sequences which are altered to yield similar secondary structure to the SL II sequence, and which bind to Rev, are "conservatively modified" variations of the SL II sequence.

The sequence of an SL II nucleic acid (SEQ ID NO:1) is:

```
GCACTATGGG CGCAGCCTCA ATGACGCTGA CGGTACAGGC CAGACAATTA

TTGTCTGGTA TAGTGC.
```

The sequence of an RRE nucleic acid (SEQ ID NO:2) is:

```
GGAGCTTTGT TCCTTGGGTT CTTGGGAGCA GCAGGAAGCA

CTATGGGCGC AGCCTCAATG ACGCTGACGG TACAGGCCAG

ACAATTATTG TCTGGTATAG TGCAGCAGCA GAACAATTTG

CTGAGGGCTA TTGAGGCGCA ACAGCATCTG TTGCAACTCA

CAGTCTGGGG CATCAAGCAG CTCCAAGCAA GAATCCTAGC

TGTGGAAAGA TACCTAAAGG.
```

Ribozymes with Rev binding nucleic acids

The Rev binding nucleic acids described above are incorporated into preferred ribozymes of the invention. Rev binding ribozymes such as the SL II nucleic acid are incorporated into preferred ribozymes at either the 3' or 5' end of the ribozyme, or both. For instance, in one preferred embodiment, the ribozyme comprises an SL II nucleic acid at the 3' terminus of the ribozyme, and an SL II nucleic acid at the 5' terminus of the nucleic acid. Examples of Rev binding ribozymes are given in SEQ ID NOs:3–7 (FIGS. 6 and 7). The given nucleic acids represent the DNA form of the active RNA, i.e., the sequences are the same as the active RNA, except that the U residues are substituted for T residues. DNA vectors which encode or express the ribozymes of the invention typically include both sense and anti-sense strands of DNA which encode the catalytically active RNA form of the ribozyme.

In one preferred embodiment, the ribozyme targets the U5 region of HIV-1, and comprises an SL II nucleic acid at the 5' end of the ribozyme. In this embodiment, the ribozyme has the sequence GCACTATGGG CGCAGCCTCA ATGACGCTGA CGGTACAGGC CAGACAATTA TTGTCTGGTA TAGTGCggat ccACACAACA AGAAGCAAC CAGAGAAACA CACGTTGTGG TATATTACCT GGTacgcgt (SEQ ID NO:3). In another preferred embodiment, the anti- U5 ribozyme has the SL II nucleic acid located at the 3' end of the ribozyme: ggatccACAC AACAAGAAGG CAACCAGAGA AACACACGTT GTG-GTATATT ACCTGGTacg cgtGCACTAT GGGCGCAGCC TCAATGACGC TGACGGTACA GGCCAGACAA TTAT-TGTCTG GTATAGTGC (SEQ ID NO:4). Note that similar ribozymes have multiple SL II nucleic acids at either the 3' or 5' end of the ribozyme, or both.

An example ribozyme which cleaves in the env/rev region of HIV-1 which incorporates the RRE at the 5' end of the ribozyme is provided by SEQ ID NO:5:

```
GGAGCTTTGT TCCTTGGGTT CTTGGGAGCA GCAGGAAGCA
CTATGGGCGC AGCCTCAATG ACGCTGACGG TACAGGCCAG
ACAATTATTG TCTGGTATAG TGCAGCAGCA GAACAATTTG
CTGAGGGCTA TTGAGGCGCA ACAGCATCTG TTGCAACTCA
CATGCTGGGG CATCAAGCAG CTCCAAGCAA GAATCCTAGC
TGTGGAAAGA TACCTAAAGG ggatcCTAGT TCCTAGAACC
AAACCAGAGA AACACACGTT GTGGTATATT ACCTGGTacg cgt.
```

A preferred ribozyme which cleaves HIV-1 targets in the env/rev region and includes an SL II sequence at the 5' end of the ribozyme is provided by SEQ ID NO:6:

```
GCACTATGGG CGCAGCCTCA ATGACGCTGA CGGTACAGGC
CAGACAATTA TTGTCTGGTA TAGTGCggat cCTAGTTCCT
AGAACCAAAC CAGAGAAACA CACGTTGTGG TATATTACCT
GGTacgcgt.
```

A preferred ribozyme which cleaves HIV-1 nucleic acids in the env/rev region, and which comprises an SL II nucleic acid at both the 3' and 5' ends of the ribozyme is provided by SEQ ID NO:7:

```
GCACTATGGG CGCAGCCTCA ATGACGCTGA CGGTACAGGC
CAGACAATTA TTGTCTGGTA TAGTGCggat cCTAGTTCCT
AGAACCAAAC CAGAGAAACA CACGTTGTGG TATATTACCT
GGTacgcgtG CACTATGGGC GCAGCCTCAA TGACGCTGAC
GGTACAGGCC AGACAATTAT TGTCTGGTAT AGTGC.
```

By convention, the above ribozyme sequences are provided as DNA sequences which have the same nucleic acid sequences as the active RNA form of the ribozyme, except that in the RNA form, the T nucleotides are replaced with U nucleotides. Lower case letters indicate restriction endonuclease cleavage sites.

Expression and Subcloning of Nucleic Acid Viral Inhibitors

Once a nucleic acid inhibitor is synthesized or cloned, one may sub clone the inhibitor or express the inhibitor in a variety of recombinantly engineered cells known to those of skill in the art. As used herein, "expression" refers to transcription of nucleic acids, with or without subsequent translation. For instance, in most embodiments of the invention, the active form of the inhibitor is an RNA molecule which acts as a molecular decoy for Rev (through binding of Rev to SL II) and as an anti-sense or ribozyme sequence which disrupts normal viral function.

Examples of cells which are suitable for the subcloning and expression of the nucleic acid inhibitors of the invention include bacteria, yeast, filarnentous fungi, insect (especially employing baculoviral vectors), and mammalian cells. It is expected that those of skill in the art are knowledgeable in the numerous expression systems available for cloning and expression of the viral inhibitors of the invention. In brief summary, the expression of natural or synthetic nucleic acids encoding viral inhibitors, is typically achieved by operably linking a nucleic acid of interest to a promoter (which is either constitutive or inducible), and incorporating the construct into an expression vector. The vectors are suitable for replication and integration in prokaryotes, eukaryotes, or both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

To obtain high levels of expression of a cloned nucleic acid it is common to construct expression plasmids which contain a strong promoter to direct transcription, a ribosome binding site for translational initiation (where a polypeptide is to be synthesized), and a transcription/translation terminator. For example, as described herein, the inhibitors of the present invention are optionally expressed in bacterial cells such as *E. coli*. Examples of regulatory regions suitable for this purpose in *E. coli* are the promoter and operator region of the *E. coli* tryptophan biosynthetic pathway as described by Yanofsky, C., 1984, *J. Bacteriol*., 158:1018–1024 and the leftward promoter of phage lambda ($P_L$) as described by Herskowitz and Hagen, 1980, *Ann. Rev. Genet*., 14:399–445. The inclusion of selection markers in DNA vectors transformed in bacteria such as *E. coli* is also useful. Examples of such markers include genes specifying resistance to ampicillin, tetracycline, or cliloramphenicol. See, Sambrook, Ausbel, and Berger for details concerning selection markers, e.g., for use in *E. coli*. Expression systems for expressing nucleic acids and polypeptides are available using *E. coli*, Bacillus sp. (Palva, I. et al., 1983, *Gene* 22:229–235; Mosbach, K. et al., *Nature*, 302:543–545) and Salmonella. *E. coli* systems are the most common, and best defined expression systems and are, therefore, preferred.

Methods of transfecting and expressing genes in eukaryotic cells are also known in the art. For example, synthesis of heterologous nucleic acids in yeast is well known and described. See, e.g., Sherman et al. (1982) *Methods in Yeast Genetics*, Cold Spring Harbor Laboratory. Examples of promoters for use in yeast include GAL1,10 (Johnson and Davies (1984) *Mol. Cell. Biol*. 4:1440–1448) ADH2 (Russell et al. (1983) *J. Biol. Chem*. 258:2674–2682), PH05 (*EMBO J*. (1982) 6:675–680), and MFαl (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids such as YEp6, YEp13, YEp4 can be used as expression vectors. These plasmids have been fully described in the literature (Botstein et al. (1979) *Gene* 8:17–24; Broach, et al. (1979) *Gene*, 8:121–133).

Two procedures are commonly used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen et al. (1978) *Proc. Natl. Acad. Sci. USA* 75:1929–1933. The second procedure does not involve removal of the cell wall. Instead the cells are treated, e.g., with lithium chloride or acetate and PEG and put on selective plates (Ito, et al. (1983) *J. Bact*. 153:163–168).

The inhibitors are isolated from yeast by lysing the cells and applying standard nucleic acid (or protein, where appropriate) isolation techniques to the lysates. The nucleic acids of this invention are purified to substantial purity by standard techniques well known in the art, including selective precipitation with such substances as ammonium sulfate, isopropyl alcohol, ethyl alcohol, column chromatography, immunopurification methods, and others. See, for instance, Sambrook supra, Ausbel supra, and Scopes (1982) *Protein Purification: Principles and Practice* Springer-Verlag New York.

Transducing cells with nucleic acids can involve, for example, incubating the cells with viral vectors (e.g., retroviral or adeno-associated viral vectors) containing nucleic acids which encode inhibitors of interest with cells within the host range of the vector. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein. The culture of cells used in conjunction with the present invention, including cell lines and cultured cells from tissue or blood samples is well known in the art. Freshney (*Culture of Animal Cells, a Manual of Basic Technique*, third edition Wiley-Liss, New York (1994)) and the references cited therein provide a general guide to the culture of cells.

Illustrative of cell cultures useful for the production of viral inhibitors include cells of insect or mammalian origin. Mammalian cell systems often will be in the form of monolayers of cells, although mammalian cell suspensions are also used. Illustrative examples of mammalian cell lines include monocytes, lymphocytes, macrophage, VERO and HeLa cells, Chinese hamster ovary (CHO) cell lines, W138, BHK, Cos-7 or MDCK cell lines (see, e.g., Freshney, supra).

As indicated above, the inhibitor, e.g., in the form of a plasmid which is used to transform a cell, preferably contains nucleic acid sequences to initiate transcription and sequences to control the translation of any polypeptide which is also encoded by the vector. These sequences are referred to generally as expression control sequences. When the host cell is of insect or mammalian origin, illustrative expression control sequences are obtained from Pol III t-RNA promoters (See, Wong-Staal et al. PCT/US94/05700) the SV-40 promoter (*Science* (1983) 222:524–527), the HIV LTR promoters, the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for inhibitor by means well known in the art.

As with yeast, when higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781).

Additionally, gene sequences to control replication in a particular host cell are incorporated into the vector, such as those found in bovine papilloma virus type-vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Va. pp. 213–238.

Host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes to containing the DNA, DEAE dextran, receptor-mediated endocytosis, electroporation and micro-injection of the DNA directly into the cells.

Transformed cells are cultured by means well known in the art. See, Freshny (supra), and Kuchler et al. (1977) *Biochemical Methods in Cell Culture and Virology*, Kuchler, R. J., Dowden, Hutchinson and Ross, Inc. The expressed nucleic acids (and polypeptides, where appropriate) are isolated from cells grown as suspensions or as monolayers. The latter are recovered by well known mechanical, chemical or enzymatic means. See, Scopes, supra.

Preferred Promoters

The inhibitors of the invention are most preferably cloned into gene therapy vectors derived from AAV or HIV for transduction of cells in vitro. In these vectors, the inhibitors are placed into expression cassettes which direct expression of the active inhibitors (SL II decoys, ribozymes, anti-sense nucleic acid, TAR decoy, transdominant gene and the like). Ideally, expression of the construct should be sufficiently high to inhibit the growth, infection or replication of the virus against which protection is sought. Accordingly, although the selection of a particular promoter is not a critical aspect of the invention, strong promoters are particularly preferred promoters for directing expression of the inhibitors in the cell. Preferred promoters include Pol III promoters such as the t-RNA promoters (e.g., the tRNA$^{Val}$ promoter; see, Wong-Staal et al. PCT/US94/05700), the HIV-2$_{KR}$ LTR promoter (See, Genbank accession No. U22047 for the complete sequence of the HIV-2$_{KR}$ virus) and strong basal promoters known to persons of skill, including cellular promoters, such as those which direct expression of the cytoskeletal machinery, such as the β-actin promoter and the tubulin promoter.

In addition to the constitutive promoters mentioned above, strong inducible promoters are also preferred. In particular, promoters which are expressed upon entry or replication of the virus in the cell are particularly preferred. For example, HIV LTR promoters are preferred promoters when the virus against which protection is sought is an HIV virus.

Measuring Viral Inhibition

The level of virus in a cell culture, cell or whole organism is measured by means known in the art. Typically, the level of virus is measured in a western blot or other immunoassay such as an ELISA, or by performing quantitative PCR. In immunoassay formats, the level of virus is measured by monitoring the amount of a viral protein (or viral capsid) by quantifying binding of the protein to an immunogenic reagent such as an antibody. In quantitative PCR, the level of a viral nucleic acid is measured by monitoring PCR amplification products, and comparing the amount of amplified nucleic acid obtained, as compared to a amplification products obtained from amplification performed on a known reference nucleic acid.

Making Antibodies

Methods of producing polyclonal and monoclonal antibodies are known to those of skill in the art, and many anti-viral antibodies are commercially available. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles*

*and Practice* (2d ed.) Academic Press, New York, N.Y.; and Kohler and Milstein (1975) *Nature* 256: 495–497. Such techniques include antibody preparation by selection of antibodies from libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

Frequently, the polypeptides and their corresponding antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

In one preferred class of embodiments, the viral proteins detected when quantifying viral inhibition in the present invention are used for the detection of the virus (such as HIV) in human (or animal, e.g., where the animal is a macaque and the virus is HIV-2 or SIV) patients. For instance, HIV polypeptides are used routinely in western blots for the detection of antibodies to HIV in a patient's blood, and the reciprocal experiment (for detecting HIV polypeptides in a patient's blood) is suitable for measuring HIV viral load in a patient's blood. Such tests are well known, and are presently a standard method by which HIV-1 and HIV-2 infections are detected in patient populations. A variety of immunoassay formats are known and available.

A particular protein can be quantified by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, N.Y.; and Ngo (ed.) (1988) *Non isotopic Immunoassays* Plenum Press, N.Y.

Immunoassays often utilize a labeling agent to specifically bind to and label the binding complex formed by the antibody and peptide or capsid. Alternatively, the labeling agent may itself be one of the antibodies. In some embodiments, the labeling agent is optionally a third moiety, such as another antibody, that specifically binds to the capture agent/polypeptide complex, or to a modified capture group (e.g., biotin) which is covalently linked to the antibody. For example, where the capture agent is a mouse antibody, the label agent may be a goat anti-mouse IgG, i.e., an antibody specific to the constant region of the mouse antibodies.

Other proteins capable of specifically binding immunoglobulin constant regions, such as streptococcal protein A or protein G are also useful as labeling agents. These proteins are normal constituents of the cell walls of streptococcal bacteria. They exhibit a strong non-immunogenic reactivity with immunoglobulin constant regions from a variety of species. See, generally Kronval, et al., (1973) *J. Immunol.*, 111:1401–1406, and Akerstrom, et al., (1985) *J. Immunol.*, 135:2589–2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentration of capture agent and analyte, and the like. Usually, the assays are carried out at ambient temperature, although they can be conducted over a range of temperatures, such as 5° C. to 45° C.

Sample Collection and Processing

An HIV transcript, antibody or polypeptide is preferably quantified in a biological sample, such as a cell, or a tissue sample derived from a patient. In a preferred embodiment, antisera to HIV polypeptides or antibodies against HIV polypeptide are quantified in serum (See, supra). In another preferred embodiment, HIV nucleic acids are detected in an infected patient using which monitor the level of viral load by hybridization to viral nucleic acids, or amplified products of viral nucleic acids. For instance, in one embodiment, HIV nucleic acids in a biological sample are amplified by an in vitro amplification technique (e.g., PCR or LCR) and detected using labeled complementary nucleic acids.

Although the sample is typically taken from a human patient, the assays can be used to detect viral polypeptides in cells from eukaryotes in general, in particular in primates such as humans, chimpanzees, gorillas, macaques, and baboons, and rodents such as mice, rats, and guinea pigs. The cells are typically part of a whole organism, or in cell culture.

The sample is pretreated as necessary by dilution in an appropriate buffer solution, or concentrated, if desired. Many standard aqueous buffer solutions employing one of a variety of buffers, such as phosphate, Tris, or the like, at physiological pH are appropriate. Cell sorting techniques such as FACS are optionally used to isolate particular cells such as $CD4^+$ cells in which the virus needs to be quantitated.

Quantification of Polypeptides, nucleic acids and Antibodies

HIV antibodies, polypeptides and nucleic acids of the invention are detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

Reduction of Non Specific Binding

One of skill will appreciate that it is often desirable to reduce non specific binding in immunoassays or nucleic acid assays, and during analyte purification. Where the assay involves a viral antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

Other Assay Formats

Western blot analysis can also be used to detect and quantify the presence of a polypeptide or antibody (including peptide, transcript, or enzymatic digestion product) in the sample. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein (antibody or HIV-2 polypeptide). The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41).

Labels

Labeling agents include e.g., monoclonal antibodies, polyclonal antibodies, proteins, or other polymers such as affinity matrices, carbohydrates or lipids. Detection proceeds by any known method, such as iminunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, Southern blotting, northern blotting, southwestern blotting, northwestern blotting, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates and immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired component of the assay according to methods well known in the art. As indicated above, a wide variety of labels are used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of antibodies. In this case, antigen-coated (e.g., HIV polypeptide-coated) particles are agglutinated by samples comprising the target antibodies. In this format, none of the components need be labeled and the presence of the target antibody is detected by simple visual inspection.

Non Therapeutic Uses of the Invention

The nucleic acids of the invention are useful as molecular probes, in addition to their utility as therapeutic agents as described herein. A wide variety of formats and labels are available and appropriate for nucleic acid hybridization, including those reviewed in Tijssen (1993) *Laboratory Techniques in biochemistry and molecular biology— hybridization with nucleic acid probes* parts I and II, Elsevier, N.Y. and Choo (ed) (1994) *Methods In Molecular Biology Volume 33- In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization" and the methods described infra for the detection of nucleic acids in general.

For instance, gel-mobility shift analysis is routinely used to detect nucleic acid-protein interactions in biological samples. Accordingly, in one class of embodiments, the inhibitors of the invention which comprise the SL II sequence are used to detect the presence of Rev in a biological sample. In this assay, the inhibitor is labeled, e.g., by radio-labeling the SL II nucleic acid, and binding of Rev to the inhibitor is monitored in a standard gel-mobility shift assay. Detection of Rev binding is an indication that the sample contains a virus such as HIV which expresses Rev. Thus, the inhibitors of the invention are, in addition to their therapeutic utility, useful as diagnostic reagents for the diagnosis of HIV infection. Wong-Staal et al. (1991) Viral And Cellular Factors that Bind to the Rev Response Element in *Genetic Structure and Regulation of HIV* (Haseltine and Wong-Staal eds.; part of the Harvard AIDS Institute Series on Gene Regulation of Human Retroviruses, Volume 1), pages 311–322 and the references cited therein describe gel mobility-shift assays for the detection of Rev in biological samples, including human blood.

Other methods for the detection of HIV nucleic acids in biological samples using nucleic acids of the invention include PCR, Southern blots, northern blots, in situ hybridization (including Fluorescent in situ hybridization (FISH), reverse chromosome painting, FISH on DAPI stained chromosomes, generation of Alphoid DNA probes for FISH using PCR, PRINS labeling of DNA, free chromatin mapping and a variety of other techniques described in Choo (supra)). A variety of automated soild-phrase detection techniques are also appropriate. For instance, large scale polymer arrays are used for the detection of nucleic acids. See, Tijssen (supra), Fodor et al. (1991) *Science*, 251: 767–777 and Sheldon et al. (1993) *Clinical Chemistry* 39(4): 718–719. The inhibitors of the invention can be adapted to use in the above assays, for example by monitoring the hybridization of the inhibitor to a viral transcript as an indicator that the viral transcript is present in a sample.

Furthermore, the inhibitors of the invention inhibit HIV infection and replication in cells which comprise the inhibitors. Therefore, one use for the inhibitors of the invention is for the diagnosis of viral infection in cells in vitro or ex vivo. In this diagnostic method, cells suspected of being infected with a particular virus are separated into two populations. The first population is transfected with a viral inhibitor of the invention which inhibits the suspected virus (e.g., in one embodiment, the suspected virus is HIV, and the inhibitor comprises an SL II sequence and an HIV ribozyme), and the second population is treated identically, except that it is not transfected (i.e., the second population is a control). If the first cell population shows enhanced viability compared to the second population, it is an indicator that the cell is infected with the particular virus.

The compositions of the invention further provide a prophylactic utility. The safety of handling and maintaining cell cultures is enhanced by incorporating the inhibitors of the invention into the cells of the cell culture, because the cells are rendered resistant to pathogenic viruses such as HIV. Because the cells are less likely to be infected with a pathogenic virus, workers handling the cells are less likely to contract the virus from the cell culture.

Vectors and Trans-complementation

Trans active genes rendered inactive in a gene therapy vector are "rescued" by trans complementation to provide a packaged vector. This form of transcomplementation is provided by vector packaging cell lines, or by co-infection of a packaging cell with a virus or vector which supplies functions missing from a particular gene therapy vector in trans. For instance, cells transduced with HIV proviral sequences which lack the nucleic acid packaging site located in and around the major splice donor site and the gag initiator codon adjacent to the 5' LTR produce HIV trans active components, but do not specifically incorporate HIV nucleic acids into the capsids produced, and therefore produce little or no live virus. If these transduced "packaging" cells are subsequently transduced with a vector nucleic acid which lacks coding sequences for HIV trans active functions, but includes an HIV packaging signal, the vector nucleic acid is packaged into an infective HIV capsid and envelope. Carrol et al. (1994) *Journal of virology* 68(9):6047–6051 describe the construction of packaging cell lines for HIV viruses.

Functions of viral replication not supplied by trans-complementation which are necessary for replication of the vector are present in the vector. In HIV, this typically includes, e.g., the TAR sequence, the sequences necessary for HIV packaging, the RRE sequence if the instability elements of the p17 gene of gag is included, and sequences encoding the polypurine tract. HIV sequences that contain these functions include a portion of the 5' long terminal repeat (LTR) and sequences downstream of the 5' LTR responsible for efficient packaging, i.e., through the major splice donor site ("MSD"), and the polypurine tract upstream of the 3' LTR through the U3R section of the 3' LTR. The packaging site (psi site or ψ site) is partially located adjacent to the 5' LTR, primarily between the MSD site and the gag initiator codon (AUG) in the leader sequence. See, Garzino-Deino et al. (1995) *Hum. Gene Ther*. 6(2): 177–184. For a general description of the structural elements of the HIV genome, see, Holmes et al. PCT/EP92/02787.

The TAR sequence is located in the R portion of the 5' LTR. It is the sequence to which the tat protein binds. The sequences necessary for packaging are located in the U5 portion of the 5' LTR and downstream of it into part of p17, as well as the U3R portion of the 3' LTR. The polypurine tract is the sequence upstream from the 3' LTR site where RNAse H cleaves during plus ("+") strand DNA synthesis. It mediates plus strand synthesis.

The primate lentiviruses, including HIV-1, HIV-2 and SIV are structurally and functionally similar. Cognate portions of any of these viruses can be used in the vectors of the present invention, or in trans-complementation assays in a manner similar to that described for HIV.

HIV virus-based vectors for use in gene therapy

Gene therapy provides a method for combating chronic infectious diseases such as AIDS, caused by HIV infection, as well as non-infectious diseases such as cancer. Yu et al. (1994) *Gene Therapy* 1:13–26 and the references therein provides a general guide to gene therapy strategies for HIV infection. See also, Sodoski et al. PCT/US91/04335. Wong-Staal et al., PCT/US94/05700 describe HIV-based gene therapy vectors, particularly HIV-1 based vectors.

The primate lentiviruses, including HIV-1, HIV-2 and SIV are structurally and functionally similar. Cognate portions of any of these viruses can be used in the vectors of the present invention, or in trans-complementation assays as set forth herein.

In brief, when constructing gene therapy vectors from a parental virus, the gene therapy vector is designed so that trans active genes rendered inactive in a gene therapy vector are capable of trans-complementation (e.g., by co-cultivation with the parental virus) in order to render the construct rescuable. This form of transcomplementation is used in creating HIV packaging cell lines and in performing co-infection assays and monitoring diagnostic assays and methods described herein. For instance, cells transduced with HIV proviral sequences which lack the nucleic acid packaging site located in and around the major splice donor site and the gag initiator codon adjacent to the 5' LTR produce HIV trans active components, but do not specifically incorporate HIV nucleic acids into the capsids produced, and therefore produce little or no live virus. If these transduced "packaging" cells are subsequently transduced with a vector nucleic acid which lacks coding sequences for HIV trans active functions, but includes an HIV packaging signal, the vector nucleic acid is packaged into an infective HIV capsid and envelope. Carrol et al. (1994) *Journal of virology* 68(9):6047–6051 describe the construction of packaging cell lines for HIV viruses.

Functions of HIV replication not supplied by transcomplementation which are necessary for replication of the vector are present in the vector. This typically includes, e.g., the TAR sequence, the sequences necessary for HIV packaging, the RRE sequence if the instability elements of the p17 gene of gag is typically included, and sequences encoding the polypurine tract. HIV sequences that contain these functions include a portion of the 5' long terminal repeat (LTR) and sequences downstream of the 5' LTR responsible for efficient packaging, i.e., through the major splice donor site ("MSD"), and the polypurine tract upstream of the 3' LTR through the U3R section of the 3' LTR. The packaging site (psi site) is partially located adjacent to the 5' LTR, primarily between the MSD site and the gag initiator codon (AUG) in the leader sequence. See, Garzino-Demo et al. (1995) *Hum. Gene Ther.* 6(2): 177–184. For a general description of the structural elements of the HIV genome, see, Holmes et al. PCT/EP92/02787.

The p17 gene contains INS (instability) elements that cause rapid degradation of the LTR promoter-mediated transcript in the absence of the Rev-RRE interaction. Therefore, if the INS sequences are included in the vector, the RRE is also typically included. However, if the HIV portion does not contain the INS sequence of p17, then the RRE sequence is optionally omitted. RRE is normally located in the envelope gene of HIV and is the sequence to which the rev protein binds.

The TAR sequence is located in the R portion of the 5' LTR. It is the sequence to which the tat protein binds. The sequences necessary for packaging are located in the U5 portion of the 5' LTR and downstream of it into part of p17, as well as the U3R portion of the 3' LTR. The polypurine tract is the sequence upstream from the 3' LTR site where RNAse H cleaves during plus ("+") strand DNA synthesis. It mediates plus strand synthesis.

Several HIV-2 isolates suitable for construction of gene therapy vectors have been isolated, including three molecular clones of HIV-2 (HIV-$2_{ROD}$, HIV-$2_{SBL-ISY}$, and HIV-$2_{UC1}$), that are reported to infect macaques (*M. mnulatta* and *M. nemestrina*) or baboons (Franchini, et al. (1989) *Proc. Natl. Acad. Sci. U.S.A.* 86, 2433–2437; Barnett, et al. (1993) *Journal of Virology* 67, 1006–14; Boeri, et al. (1992) *Journal qf Virology* 66, 4546–50; Castro, et al. (1991) *Virology* 184, 219–26; Franchini, et al. (1990) *Journal of Virology* 64, 4462–7; Putkonen, et al. (1990) *Aids* 4, 783–9; Ptitkonen, et al. (1991) *Nature* 352, 436–8). HIV-$2_{KR}$ (see supra) also infects macaques and human cells, and gene therapy vectors using the HIV-$2_{KR}$ LTR regions are one class of preferred gene therapy vectors. Another class of preferred gene therapy vectors includes HIV-1 LTR sequences.

Murine Retroviral Vectors

Murine retroviral vectors are known in the art. The majority of the approved gene transfer trials in the United States rely on replication-defective retroviral vectors derived from murine retroviruses such as murine moloney retrovirus (referred to alternately as MoLv MoMuLv or MuLv in the art). See Miller et al. (1990) *Mol. Cell. Biol.* 10:4239; Kolberg R (1992) *J. NIH Res.* 4:43, and Cornetta et al. (1991) *Hum. Gene Ther.* 2:215. The major advantages of murine retroviral vectors for gene therapy are the high efficiency of gene transfer into certain types of replicating cells, the precise integration of the transferred genes into cellular DNA, and the lack of further spread of the sequences after gene transfer.

AAV Vectors

Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993) *Current Opinion in Genetic and Development* 3:74–80 and the references cited therein provides an overview of the AAV life cycle.

AAV-based vectors are used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors.

Recombinant AAV vectors (rAAV vectors) deliver foreign nucleic acids to a wide range of mammalian cells (Hermonat & Muzycka (1984) *Proc Natl Acad Sci USA* 81:6466–6470; Tratschin et al. (1985) *Mol Cell Biol* 5:3251–3260), integrate into the host chromosome (Mclaughlin et al. (1988) *J Virol* 62: 1963–1973), and show stable expression of the transgene in cell and animal models (Flotte et al. (1993) *Proc Natl Acad Sci USA* 90:10613–10617). Moreover, unlike some retroviral vectors, rAAV vectors are able to infect non-dividing cells (Podsakoff et al. (1994) *J Virol* 68:5656–66; Flotte et al. (1994) *Am. J. Respir. Cell Mol. Biol.* 11:517–521). Further advantages of rAAV vectors include the lack of an intrinsic strong promoter, thus avoiding possible activation of downstream cellular sequences, and their naked icosohedral capsid structure, which renders them stable and easy to concentrate by common laboratory techniques. rAAV vectors are used to inhibit, e.g., viral infection, by including anti-viral transcription cassettes in the rAAV vector which comprise an inhibitor of the invention.

Viral Inhibitors and Gene Therapy

Common gene therapy vectors include those derived from inurine retroviruses (including MuLv), avian rous sarcoma virus (RSV), Hepatocyte viruses, HIV-1, HIV-2 and AAV-based vectors. HIV based vectors and AAV based vectors are preferred, because they do not require actively dividing cells for infection (unlike many murine retroviruses). HIV vectors are most preferred for treating HIV infections, because they typically only infect CD4$^+$ cells in vivo, i.e., those cells which are infected by HIV viruses.

The present invention provides several features that allow one of skill to generate powerful retroviral gene therapy vectors against specific cellular targets, in vitro and in vivo, e.g., against CD4$^+$ cells. CD4$^+$ cells are infected by HIV viruses (including HIV-1 and HIV-2). HIV viruses also infect a few other cell-types in vitro which exhibit little or no CD4 expression, such as peripheral blood dendritic cells, follicular dendritic cells, epidermal Langerhans cells, inegakaryocytes, microglia, astrocytes, oligodendroglia, $CD8^+$ cells, retinal cells, renal epithelial cells, cervical cells, rectal mucosa, trophoblastic cells, and cardiac myocytes (see, Rosenburg and Fauci 1, supra); the infection of these cell types by HIV in vivo, however, is rare. Lists of $CD4^+$ and $CD4^-$ cell types which are infectable by HIV have been compiled (see, Rosenburg and Fauci 1 supra; Rosenburg and Fauci (1989) *Adv Ininiunol* 47:377–431; and Connor and Ho (1992) in *AIDS: etiology, diagnosis, treatment, and prevention*, third edition Hellman and Rosenburg (eds) Lippincott, Philadelphia).

The present invention provides viral inhibitors which comprise Rev binding nucleic acids such as SL II nucleic acids. These nucleic acids are useful as components of gene therapy vectors. Retroviral vectors packaged into HIV envelopes primarily infect $CD4^+$ cells, (i.e., by interaction between the HIV envelope glycoprotein and the CD4 "receptor") including non-dividing $CD4^+$ cells such as macrophage. For instance, nucleic acids which encode viral inhibitors are encapsidated into HIV capsids in gene therapy vectors which include an HIV packaging site (e.g., the ψ site in HIV-1), and typically also include the HIV LTR sequences. Thus, in one preferred embodiment, the inhibitors of the present invention are incorporated into HIV-based gene therapy vectors which deliver the inhibitors to $CD4^+$ cells in a form which results in stable integration and expression of the inhibitor into the cell. This is accomplished by incorporating cis active nucleic acids (e.g., promoter sequences, packaging sequences, integration or cellular targeting sequences) into the vector, or by using trans active nucleic acids and polypeptides (capsid and envelope proteins and transcription factors) to replicate and package the gene therapy vector into an viral capsid (e.g., an HIV-1 or HIV-2 capsid and envelope), or both. See, e.g., Poznansky et al. (1991) *Journal or Virology* 65(1): 532–536 and Garzino Dem et al. (supra) for a description of the ability of the region flanking the 5' HIV LTR.

A preferred class of embodiments utilizes $HIV-2_{KR}$ LTR sequences as a component of a gene therapy vector. The LTR sequences of $HIV-2_{KR}$ are particularly useful, because they have a high level of basal promoter activity in CD4 cells, and have no tat or rev requirement for transactivation.

In one embodiment, the inhibitors of the present invention comprise antisense nucleic acids which specifically hybridize to a viral nucleic acid, thereby inhibiting the activity of the nucleic acid. Wong-Staal et al. PCT application PCT/US94/05700 (WO 94/26877) and Chatterjee et al. (*Science* (1992), 258: 1485–1488, hereinafter Chatterjee et al. 1) describe anti-sense inhibition of HIV-1 infectivity in target cells using viral vectors with a constitutive expression cassette expressing anti-TAR RNA. Chatterjee et al. (PCT application PCT/US91/03440 (1991), hereinafter Chatterjee et al. 2) describe viral vectors, including AAV-based vectors which express antisense TAR sequences. Chatterjee and Wong (*Methods, A companion to Methods in Enzymology* (1993), 5: 51–59) further describe viral vectors for the delivery of antisense RNA. Yu et al. (1994) *Gene Therapy* 1: 13–26 and the references cited therein provides a general guide to gene therapy strategies useful against HIV infection.

Ex Vivo Therapy

Ex vivo methods for inhibiting viral replication in a cell in an organism involve transducing the cell ex vivo with a vector of this invention, and introducing the cell into the organism. Cells are typically selected based upon the host range of the virus against which an inhibitor is directed. For instance, where the virus is an HIV virus, the cells selected for transfection are typically $CD4^+$ cells such as $CD4^+$ T cells, or $CD4^+$ macrophage isolated or cultured from a patient. Stem cells (e.g., CD34+ cells) are particularly preferred target cells for transduction and use in ex vivo gene therapy procedures. See, e.g., Freshney et al., supra. and the references cited therein, and the discusion provided herein for a discussion of how to isolate and culture cells from patients. Alternatively, the cells can be those stored in a cell bank (e.g., a blood bank). In one class of preferred embodiments, the gene therapy vector utilizes an inhibitor which includes an SL II nucleic acid, and an anti-viral therapeutic agent (e.g., transdominant gene, ribozyme, antisense gene, and/or decoy gene) which inhibits the growth or replication of a virus (e.g., and HIV virus such as HIV-1). The gene therapy vector inhibits viral replication in any of those cells already infected with the virus, in addition to conferring a protective effect to cells which are not infected by the virus.

In addition, in preferred embodiments, the vector is replicated and packaged into viral capsids such as HIV capsid/envelopes using the viral replication machinery. Typically, the necessary functions for encapsidation of the vector are supplied in trans by a parental virus which recognizes and packages nucleic acids which contain appropriate packaging sequences.

Thus, a patient infected with a virus such as HIV-1 can be treated for the infection by transducing a population of their cells with a vector of the invention and introducing the transduced cells back into the patient as described herein. Thus, the present invention provides a method of protecting cells in vitro, ex vivo or in vivo, and the cells are optionally already infected with the virus against which protection is sought.

In Vivo Therapy

Gene therapy vectors containing nucleic acids of the invention can be administered directly to the organism for transduction of cells in vivo. Administration of gene therapy vectors comprising the viral inhibitors of the invention, and cells transduced with the gene therapy vectors is by any of the routes normally used for introducing a molecule into ultimate contact with blood or tissue cells. As described herein, preferred vectors utilize HIV viral particles, but other arrangements are also feasible, such as adeno-associated capsids, naked DNA or RNA forms of the gene therapy vectors, or any of the numerous vectors known in the art (see, supra.). Gene therapy vectors and cells of the present invention can be used to treat and prevent virally-mediated diseases such as AIDS in patients.

The vectors or cells are administered in any suitable manner, preferably with pharmaceutically acceptable carriers. Suitable methods of administering such vectors or cells in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The vectors, alone or in combination with other suitable components, can be made into aerosol formulations to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the vector with a suppository base. Suitable suppository bases include natural or synthetic triglycerides or paraffin hydrocarbons. In addition, it is also possible to use gelatin rectal capsules which consist of a combination of the vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous administration is the preferred method of administration for gene therapy vectors and transduced cells of the invention. The formulations of vector can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. For many vectors, this mode of administration will not be appropriate, because many virions are destroyed by lyophilization. Other vectors (e.g., vectors utilizing an AAV capsid, or naked nucleic acids) tolerate lyophilization well.

Extemporaneous injection solutions and suspensions can be prepared from sterile powders, granules, and tablets of the kind previously described. Cells transduced by the vector, e.g., as described above in the context of ex vivo therapy, can also be administered parenterally as described above, except that lyophilization is not generally appropriate, since cells are destroyed by lyophilization.

The dose administered to a patient, in the context of the present invention should be sufficient to effect a beneficial therapeutic response in the patient over time, or to inhibit infection by a pathogenic strain of HIV. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient. In determining the effective amount of the vector to be administered in the treatment or prophylaxis of virally-mediated diseases such as AIDS, the physician needs to evaluate circulating plasma levels, vector toxicities, progression of the disease, and the production of anti-HIV antibodies. In general, the dose of a naked nucleic acid composition such as a DNA is from about 1 $\mu$g to 100 $\mu$g for a typical 70 kilogram patient, and doses of gene therapy vectors which include viral capsids such as AAV or HIV vectors are calculated to yield an equivalent amount of inhibitor nucleic acid.

In the practice of this invention, compositions can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions. The vectors of this invention can supplement treatment of virally-mediated conditions by any known conventional therapy, including cytotoxic agents, nucleotide analogues and biologic response modifiers.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are provided by way of illustration only and not by way of limitation. Those of skill will readily recognize a variety of noncritical parameters which could be changed or modified to yield essentially similar results.

Materials and Methods

The following materials and methods were used in the examples below.

Construction of chimeric stem-loop II RRE/ribozyme vectors pMJT and pOY-1 are Moloney murine leukemia virus vectors carrying either the HIV-1 5' leader sequence specific ribozyme (anti-U5 ribozyme) or the HIV-1 Rev sequence specific ribozyme (anti-Rev ribozyme), respectively, driven by the internal human t-RNA$^{val}$ promoter (Yamada et al., *Virology* (1994) 205:121–126; Yu et al., *Proc Natl. Acad. Sci. USA* (1993) 90:6340–6344). pdMJT is a construct containing the disabled form of the anti-U5 ribozyme, with the CGU at position 24–26 replaced by AAA (Ojwang et al., *Proc. Natl. Acad. Sci. USA.* (1992) 89:10802–10806). The stem-loop II sequences of RRE in HIV-1 MN (7824–7889) were amplified by PCR with the primer pair 5' SL2 (5'-agagatct GCA CTA TGG GCG CAG C-3'; SEQ ID NO:9) and 3'rcSL2 (5'-cgggatcc GCA CTA TAC CAG ACA AT-3'; SEQ ID NO:10). The PCR product was digested with Bam HI/Bgl II and then ligated with Bam HI-digested pMJT. After transformation with this plasmid into the *E. coli* strain DH5$\alpha$, a clone in which the SL II was linked to the ribozyme sequence in the same orientation was obtained by screening. The ribozyme sequences in this plasmid, designated as pSLMJT, were replaced with the disabled ribozyme or anti-Rev ribozyrne at the Bam HI/Mlu I to generate pSLd-MJT or pSLOY-1, respectively.

Generation of Stable cell lines

Molt-4/8 cells were transfected with the parental vector, pMJT, pOY-1, pdMJT, pSLMJT, pSLOY-1 or pSLdMJT by the liposome-mediated method using DOTAP (Boehringer Mannheim). Transfected cells were selected by growth in G418 (GIBCO) supplemented media as described previously. Resistant Molt-4/8 cells were designated as MLNL6, MMJT, MOY-1, MdMJT, MSLMJT, MSLOY-1 and MSLdMJT, respectively.

HIV-1 SF2 infection of MOY-1 and MSLOY-1 cells

G418 selected MOY-1, MSLOY-1, and parental Molt-4/8 cells were incubated with infectious HIV-1 SF2 at an input M.O.I. of 0.01 for 2 hr and washed twice. These cells were cultured at an initial concentration of $10^5$ cells/ml in RPMI1640 medium supplemented with 10% fetal calf serum (FCS). On days 5 and 8 after infection, the infected cells were split 1:5 with medium to adjust to a cell concentration of approximately $2\times10^5$/ml. The culture supernatants were collected on days 3, 5, 8, and 11 after infection, and the level of HIV-1 p24 antigen was determined by the HIV-1 antigen capture ELISA test (Coulter).

Cocultivation of the stable cell lines with HXB2 infected Jurkat cells

Jurkat cells chronically infected with HIV-1 HXB2 were washed twice with RPMI 1640. One hundred or one thousand of these cells were suspended in 1 ml of RPMI1640 supplemented with 10% FCS and containing $10^5$ cells each of the stably transduced cell lines. On day 4 after infection, the cells were split to adjust the cell concentration to approximately $2\times10^5$/ml and the cells were split 1:5 with medium every 3 days thereafter. The culture supernatants were used for measurement of p24 antigen by the HIV antigen capture ELISA test (Coulter).

Quantitative Conmpetitive (QC) RT PCR

Total cellular RNA was extracted from ribozyme-transduced cells or parental Molt-4/8 cells by the guanidine thiocyanate-phenol/chloroform extraction method (Chomczynski et al., Anal Biochem. (1987) 162:156–159) and subsequently treated with deoxyribonuclease I (RQI DNase; Promega) as previously described (Yamada et al., Gene Therapy (1994) 1:38–45). For QC-RT PCR, in vitro transcribed RNA of the anti-U5 ribozyme with a tetraloop substitution (5'-ACA CAA CAA GAA GGC AAC CAG AGA AAC ACA CGG ACU UCG GUC CGU GGU AUA UUA CCU GGU A-3'; SEQ ID NO:11) was used as competitor RNA. Total cellular RNA (0.5 mg) and the competitive RNA diluted 10 fold serially (10 fg to 10 pg) were added to the RT reaction mixture (final volume, 16 μl) containing 10 mM Tris-HCl (pH 8.3), 90 mM KCl, 1 mM MnCl$_2$, 200 mM each of dATP, dGTP, dCTP, and dTTP, 50 p moles of Rib 2 and 3 units of Tth DNA polymerase (Promega). After the RT reaction at 60° C. for 20 min, 34 μl of PCR buffer containing 25 mM Tris-HCl, 1.1 mM EGTA, 200 mM KCl, 3.75 mM MgCl$_2$, 50 pmoles of Rib 4 (Yamada et al., Gene Therapy (1994) 1:38–45), and 200 mM each of dATP, dGTP, dCTP, and dTTP was added to each tube and PCR was carried out (94° C. 30s, 50° C. 30s, 72° C. 30s, 30 cycles). Ten μl of each PCR product was subjected to agarose gel (5% low melting agarose) electrophoresis. The expected sizes of the amplified products were 61 bp and 52 bp, respectively, for the competitor RNA and the test RNA. Gel-images after staining with ethidium bromide were scanned by Twain Scan Duo 600 (Mustek) using Color it v3.0 and analyzed using NIH image v.1.54 by Macintosh computer.

Quantitative Competitive (QC) PCR $10^6$ cells each of MMJT, MdMJT, MSLMJT, or MSLdMJT were suspended in one ml of a DNase treated HIV-1 HXB2 preparation ($10^{5.25}$TCID$_{50}$/ml) in a 1.5 ml tube. The infected cells were incubated for 7 h at 37° C. and washed two times with RPMI 1640 medium. Five hundred μl of lysis buffer containing 50 mM Tris, 40 mM KCl, 1 mM dithiothreitol, 6 mM MgCl$_2$, 0.45% NP40, and 200 mg/ml proteinase K was added to each tube and incubated for 2 h at 50° C. The cell-lysates were heated for 10 min in boiling water and used as template DNA for QC-PCR. In the QC-PCR, a 5' primer, $^{32}$P-end-labeled-SK29 (corresponding to nt 501–518 in the LTR) and a 3' primer, SK30 (corresponding to nt 605–589 in the LTR) (Ou et al., Science (1988) 239:295–297) was used.

Competitor DNA was prepared as follows: PCR was carried out with HXB2 DNA as template using a 5' primer, X+5' LTR, which has 18 random bases (X sequences) flanking the 5' end of the HXB2 LTR 516–534 (5'-gat agc ggg tag cta gat GCT TAA GCC TCA ATA AAG C-3'; SEQ ID NO:12) and a 3' primer, SK 30. The PCR product was reamplified with a 5' primer, SK29+X, which contains X sequences immediately 3' end of the region corresponding to SK29 (5'-ACT AGT GAA CCC ACT GCT gat agc ggg tag cta gat g-3'; SEQ ID NO:13) and a 3' primer, SK 30. The reamplified product was cloned into pUC 19 at the Sma I site and the resultant plasmid (pUC SK29+X/SK30) was used as competitor DNA. Twenty-five μl each of the cell-lysate and 5 μl each of different concentrations ($10^3$ to $10^5$ copies in 5 μl) of the competitor DNA preparation were added to each 0.5 ml tube containing the reaction mixture (total volume 50 μl). The composition of the reaction mixture for the PCR was 50 mM Tris-HCl (pH 8.3), 3 mM MgCl2, 40 mM KCl, 1 mM dithiothreitol, 200 mM each of dATP, dGTP, dCTP, and dTTP, and 2.5 pmoles of SK29 (5–7.5×$10^5$ c.p.m.). Condition of the amplification was 95° C./30s; 50° C./30s; 72° C./30s for 25 cycles. Taq polymerase (1.25 units; Promega) was added to each reaction tube after the first denaturation step (95° C./30s). The expected sizes of the amplified products were 105 bp and 123 bp for the test PCR product and the competitor DNA product, respectively. After PCR, 3 μl each of the PCR products were loaded onto an 8% polyacrylamide gel and autoradiographed. Images of the gel were scanned by Twain Scan Duo 600 (Mustek) with Color it v3.0. The signal-intensity of the competitor and test PCR products was analyzed using NIH image v.1.54 and by Macintosh computer.

Example 1

RRE decoy effect of the SL II-ribozyme fusion RNA

Figure 1A:
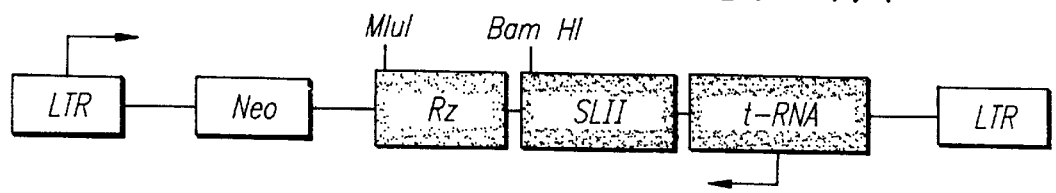
FIGS. 1A–1C panel (A) is a schematic representation of the retroviral vectors expressing anti-HIV-1 ribozyme (Rz)
Figure 1B:
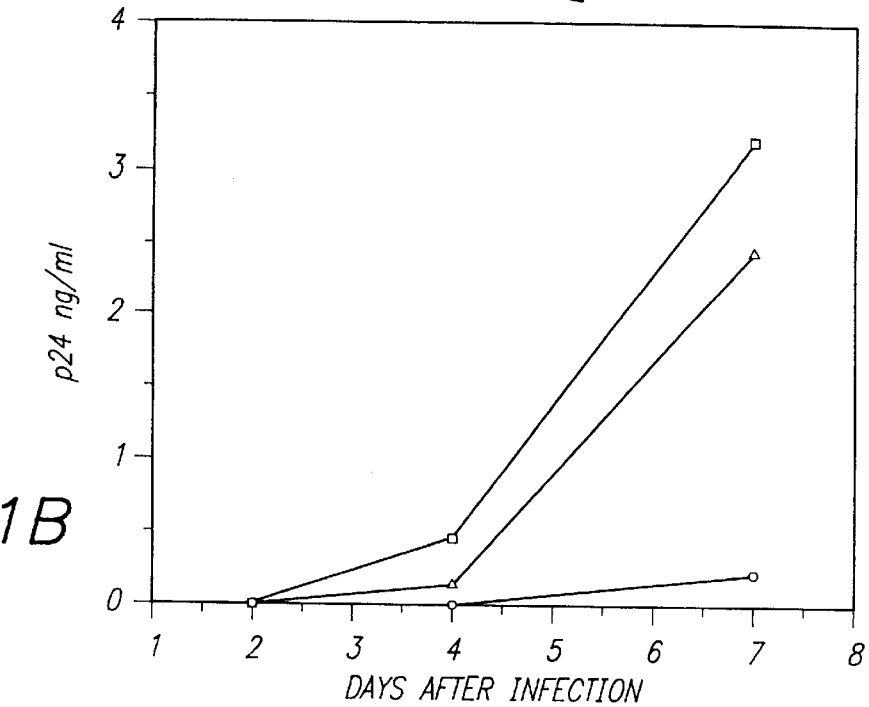
Figure 1C:
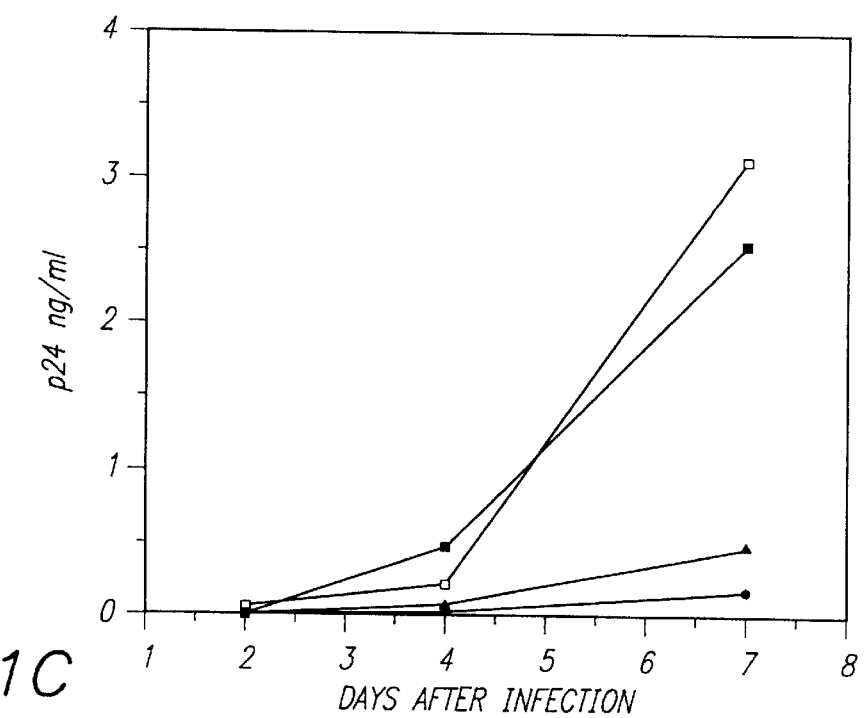
Figure 2A:
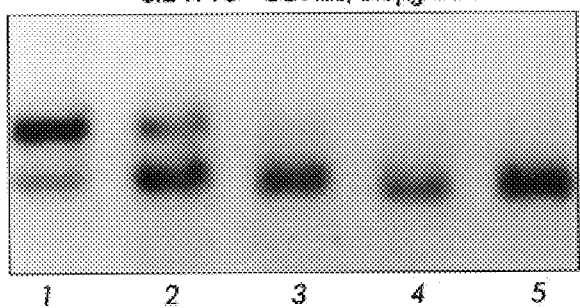
Figure 2B:
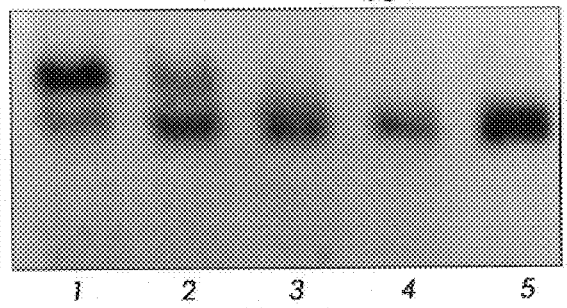
Figure 2C:
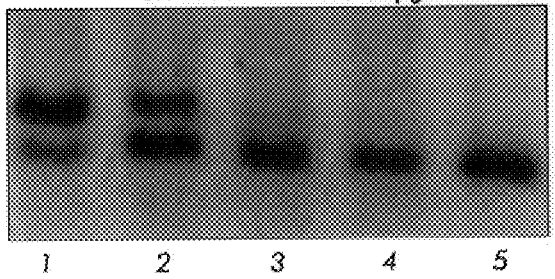
Figure 2D:
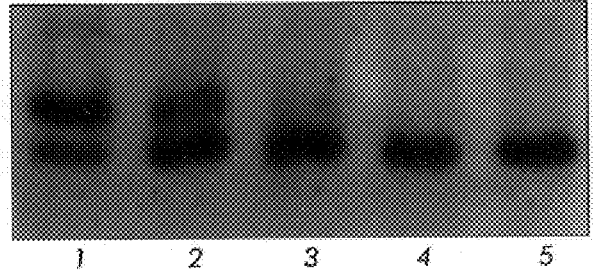

To specifically examine the RRE decoy effect of an SL II-hairpin ribozyme fusion RNA, HIV-1 SF2 was used as a challenge virus for cells expressing anti-U5 and anti-Rev ribozymes fused to SL II (FIG. 1A). It was previously reported that the HIV-1 SF2 virus is refractory to the anti-Rev (OY-1) ribozyme because of a single nucleotide substitution of G→U at the cleavage site (Yamada et al., Virology (1994) 205:121–126), while the U5 target sequence is conserved in this virus. Expression of the anti-Rev ribozyme in the MOY-1 cells and the MSLOY-1 cells was observed by RT-PCR as previously described (Yamada et al., Gene Therapy (1994) 1:38–45). As shown in FIG. 1B, only marginal protection against SF2 infection was shown in the MOY-1 cells compared with Molt-4/8, consistent with previous data. However, expression of p24 antigen of HIV-1 was not detected in the MSLOY-1 cells. Thus, the protection in the MSLOY-1 cells was due to an RRE decoy effect of the fusion molecule. In contrast, HIV-1$_{SF}$ expression was inhibited in both MMJT and MSLMJT cells, expressing either the anti-U5 ribozyme or the SL II-anti U5 ribozyme fusion molecule (FIG. 1C).

Example 2

Quantitation of Anti-U5 Ribozyme Expression in Stable Cell Lines

Expression of the ribozyme or disabled ribozyme in MJT, dMJT, MSLMJT, and MSLdMJT cells was examined by RT-PCR as described herein, using the Rib 4/2 primer pair and oligonucleotide probes that would selectively detect the functional or the disabled ribozyme. Amplified products were specifically detected only when PCR was carried out after reverse transcription. Using a 5' primer corresponding to the SL II sequence, expression of the SL II-ribozyme fusion RNA was detected at 25 weeks after transfection in both cell lines. The expression levels of the ribozyme in the stable cell lines were then examined by QC-RT PCR using the Rib 4 and Rib 2 primer pair. FIG. 2 shows the inverted gel images after staining with ethidium bromide. The number of competitor RNA molecules that result in equal signal-intensity of the amplified products of competitor and test RNA was calculated from regression line by the least-squares method. The ribozyme expression level was thus estimated to be $5.3 \times 10^7 - 6.2 \times 10^7$ copies/0.5 mg of total cellular RNA in the four cell lines examined (FIG. 2). Since the amount of total cellular RNA is generally assessed at 1 mg RNA/$10^5$ cells, it is estimated that each cell was expressing approximately 1000–1200 copies of ribozyme containing RNA.

These constitutive levels of ribozyme or fusion RNA expression had no apparent deleterious effect on the Molt 4/8 cells, as all transfected cell lines and parental Molt 4/8 cells were indistinguishable with respect to cell-growth rate and viability over a period of six months, with passage of the cells every 4 days.

Example 3

Protection against cell-cell transmission of HIV-1/HXB2 in the fusion RNA-expressing cells The relative antiviral potency of the ribozyme and the SL II/U5 ribozyme vectors was compared in a system utilizing cell-associated virus as the challenge agent. Jurkat cells chronically infected with HIV-1 /HXB2 were cocultured with stable ribozyme-expressing cell lines at different ratios for infection (1000:1 and 100:1 uninfected to infected cells). Low levels of p24 expression was detected in all cultures early, i.e., from the infected Jurkat cells directly. The expression of p24 in the MdMJT and MLNL6 increased sharply at day 25 (FIG. 3A) at 1000:1 infection or at day 19 at 100:1 infection (FIG. 3B). Emergence of virus expression in MMJT and MSLdMJT cells was delayed to day 31 at 1000:1 infection, or day 25 at 100:1 infection. Thus, a single antiviral gene (ribozyme or SL II decoy) had a detectable, inhibitory effect on viral replication. Furthermore, the p24 level was kept at a low level in MSLMJT (ribozyme+SL II) at 1000:1 infection during the entire culture period of 34 days (FIG. 3A). Even at 100:1 infection, the increase in p24 level of MSLMJT was delayed for an additional 3 days (to day 28) compared to MMJT or MSLdMJT. These results indicated that the combination of the SL II and ribozyme was more effective than either the ribozyme or SL II decoy alone in the inhibition of HIV-1 .

Example 4

Comparison of the ribozyme activity in MMJT and MSLMJT in a first round infection To examine the ribozyme activity of the fusion RNA, the reduction in proviral DNA synthesis was measured in the first round of replication after viral challenge. The RRE decoy effect is not relevant in this early part of the replication cycle. The proviral DNA level in the stable cell lines was quantified by competitive PCR 7 hours after challenge with HIV-1/HXB2. Proviral DNA was amplified in the presence of different concentrations of competitor DNA using $^{32}$P-end labeled-SK29/SK30 as the primer pair. The autoradiograph after QC-PCR and the results after analysis of the gel images were shown in FIG. 4A and 4B, respectively. The number of molecules of added competitor DNA which results in equal signal intensity of the amplified products from the test and competitor DNA was estimated from the regression line by the least-squares method, and should correspond to the proviral DNA copy number in $2 \times 10^5$ cells. As expected, no difference in the proviral DNA copy number was observed between MdMJT and MSLdMJT, suggesting a lack of effect of the RRE decoy on preintegration events. The DNA copy number for MSLMJT was reduced to 1/7 of that for MSLdMJT, whereas that for MMJT was reduced to 1/3. Similar QC-PCR using a primer pair for β-globin DNA confirmed that an equal number of cells were used to generate the cell lysate for the quantitative analyses. This experiment was repeated with similar results. Consequently, the results demonstrated that the SL II-ribozyme fusion RNA indeed functioned as a ribozyme, and the reproducible difference observed between MSLMJT and MJT cells suggested that the linkage of the SL II sequence further improved the ribozyme activity. The reduction in DNA level in MMJT cells was 10–20 times less than the result described in a previous paper (Yamada et al., *Gene Therapy* (1994) 1:38–45). This may be due to the fact that a 20-fold higher M.O.I. (0.2 instead of 0.01) was used for infection in the present study.

All publications and patent applications cited in this specification are herein incorporated by reference for all purposes as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A molecule selected from a trans-active ribozyme which hybrdizes to a nucleic acid of a Rev-binding primate lentivirus, wherein said trans-active ribozyme comprises a Rev-binding nucleic acid which is less cytotoxic than a full-length Rev response element, and a molecule which encodes a trans-active ribozyme which hybridizes to a nucleic acid of a Rev-binding primate lentivirus, wherein said trans-active ribozyme comprises a Rev-binding nucleic acid which is less cytotoxic than a full-length Rev response element.

2. The molecule of claim 1, which is a trans-active ribozyme, wherein said trans-active ribozyme comprises a Rev-binding nucleic acid which is less cytotoxic than a full-length Rev response element.

3. The molecule of claim 2, wherein said Rev-binding nucleic acid is an SL II nucleic acid.

4. The molecule of claim 2 wherein said SL II nucleic acid comprises the nucleic acid of SEQ ID NO: 1.

5. The molecule of claim 2, wherein said ribozyme is a hairpin ribozyme.

6. The molecule of claim 2, wherein said ribozyme comprises a plurality of Rev-binding nucleic acids.

7. The molecule of claim 2, wherein said ribozyme comprises an SL II nucleic acid at the 3' terminus of the ribozyme and a second SL II nucleic acid at the 5' terminus of the ribozyme.

8. The molecule of claim 2 wherein said ribozyme has a sequence selected from the group of SEQ ID NO:3, SEQ ID NO:4, SEQ ID NO:5, SEQ ID NO:6, and SEQ ID NO:7.

9. The molecule of claim 2, wherein said ribozyme cleaves an HIV-1 nucleic acid in a cell culture.

10. The molecule of claim 1, which encodes a trans-active ribozyme which hybridizes to a Rev-binding primate lentivirus nucleic acid, wherein said trans-active ribozyme comprises a Rev-binding nucleic acid which is less cytotoxic than a full-length Rev response element.

11. The molecule of claim 10, wherein said molecule is a targeted HIV chimeric nucleic acid, and wherein said trans-active ribozyme cleaves an HIV nucleic acid and provides greater viral inhibition as compared to a ribozyme which cleaves the same site of said HIV nucleic acid but which lacks a Rev-binding nucleic acid sequence.

12. The molecule of claim 10 wherein said molecule, when transfected into a cell culture and expressed in the cell culture, provides inhibition of a Rev-binding primate lentivirus in the cell culture for more than 15 weeks after the transfection.

13. The molecule of claim 10, wherein said molecule, when transfected into a cell culture and expressed in the cell culture, is not cytotoxic for at least 15 weeks following transfection.

14. The molecule of claim 10, wherein said trans-active ribozyme is a hairpin ribozyme.

15. The molecule of claim 10, wherein said molecule further comprises an anti-sense nucleic acid which specifically hybridizes to a nucleic acid encoded by the Rev-binding primate lentivirus.

16. A molecule comprising a trans-acting ribozyme and an SL II nucleic acid, which molecule inhibits replication of a Rev-binding primate lentivirus in eukaryotic cells in cell culture.

17. The molecule of claim 16, which molecule further comprises an anti-sense nucleic acid which specifically hybridizes to a nucleic acid encoded by the Rev-binding primate lentivirus.

18. The molecule of claim 16, wherein said molecule comprises a plurality of SL II nucleic acids.

19. A recombinant transcription cassette comprising the molecule of claim 10.

20. A vector comprising the molecule of claim 10, wherein said vector further comprises nucleic acids selected from the group consisting of the HIV packaging site and the AAV ITR.

21. A recombinant eukaryotic cell in culture which comprises a molecule which encodes a trans-active ribozyme which hybridizes to a nucleic acid of a Rev-binding primate lentivirus, wherein said trans-active ribozyme comprises a Rev-binding nucleic acid which is less cytotoxic than a full-length Rev response element.

22. The recombinant eukaryotic cell of claim 21, wherein said Rev-binding nucleic acid is an SL II nucleic acid.

23. The recombinant eukaryotic cell of claim 21, wherein said molecule, when expressed in a cell culture in vitro, provides viral inhibition to the cell culture for more than 15 weeks.

24. A recombinant eukaryotic cell in culture which stably expresses a molecule which molecule comprises an SL II nucleic acid and a trans-active ribozyme which hybridizes to a nucleic acid of a Rev-binding primate lentivirus.

25. The cell of claim 24 wherein said cell is a $CD4^+$ cell selected from the group consisting of monocytes, lymphocytes and macrophages.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:1:

GCACTATGGG CGCAGCCTCA ATGACGCTGA CGGTACAGGC CAGACAATTA TTGTCTGGTA     60

TAGTGC     66

(2) INFORMATION FOR SEQ ID NO:2:

(i) SEQUENCE CHARACTERISTICS:
            (A) LENGTH: 220 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

GGAGCTTTGT TCCTTGGGTT CTTGGGAGCA GCAGGAAGCA CTATGGGCGC AGCCTCAATG     60

ACGCTGACGG TACAGGCCAG ACAATTATTG TCTGGTATAG TGCAGCAGCA GAACAATTTG    120

CTGAGGGCTA TTGAGGCGCA ACAGCATCTG TTGCAACTCA CAGTCTGGGG CATCAAGCAG    180

CTCCAAGCAA GAATCCTAGC TGTGGAAAGA TACCTAAAGG                          220

(2) INFORMATION FOR SEQ ID NO:3:

(i) SEQUENCE CHARACTERISTICS:
            (A) LENGTH: 129 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:3:

GCACTATGGG CGCAGCCTCA ATGACGCTGA CGGTACAGGC CAGACAATTA TTGTCTGGTA     60

TAGTGCGGAT CCACACAACA AGAAGGCAAC CAGAGAAACA CACGTTGTGG TATATTACCT    120

GGTACGCGT     129

(2) INFORMATION FOR SEQ ID NO:4:

(i) SEQUENCE CHARACTERISTICS:
            (A) LENGTH: 129 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

GGATCCACAC AACAAGAAGG CAACCAGAGA AACACACGTT GTGGTATATT ACCTGGTACG     60

CGTGCACTAT GGGCGCAGCC TCAATGACGC TGACGGTACA GGCCAGACAA TTATTGTCTG    120

```
GTATAGTGC                                                                   129
```

(2) INFORMATION FOR SEQ ID NO:5:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
GGAGCTTTGT TCCTTGGGTT CTTGGGAGCA GCAGGAAGCA CTATGGGCGC AGCCTCAATG    60

ACGCTGACGG TACAGGCCAG ACAATTATTG TCTGGTATAG TGCAGCAGCA GAACAATTTG   120

CTGAGGGCTA TTGAGGCGCA ACAGCATCTG TTGCAACTCA CAGTCTGGGG CATCAAGCAG   180

CTCCAAGCAA GAATCCTAGC TGTGGAAAGA TACCTAAAGG GGATCCTAGT TCCTAGAACC   240

AAACCAGAGA ACACACGTT GTGGTATATT ACCTGGTACG CGT                     283
```

(2) INFORMATION FOR SEQ ID NO:6:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
GCACTATGGG CGCAGCCTCA ATGACGCTGA CGGTACAGGC CAGACAATTA TTGTCTGGTA    60

TAGTGCGGAT CCTAGTTCCT AGAACCAAAC CAGAGAAACA CACGTTGTGG TATATTACCT   120

GGTACGCGT                                                           129
```

(2) INFORMATION FOR SEQ ID NO:7:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
GCACTATGGG CGCAGCCTCA ATGACGCTGA CGGTACAGGC CAGACAATTA TTGTCTGGTA    60

TAGTGCGGAT CCTAGTTCCT AGAACCAAAC CAGAGAAACA CACGTTGTGG TATATTACCT   120

GGTACGCGTG CACTATGGGC GCAGCCTCAA TGACGCTGAC GGTACAGGCC AGACAATTAT   180

TGTCTGGTAT AGTGC                                                    195
```

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:8:

```
NNNSNGUCNN NNNNNN                                                    16
```

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
AGAGATCTGC ACTATGGGCG CAGC                                    24
```

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
CGGGATCCGC ACTATACCAG ACAAT                                   25
```

(2) INFORMATION FOR SEQ ID NO:11:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:11:

```
ACACAACAAG AAGGCAACCA GAGAAACACA CGGACUUCGG UCCGUGGUAU AUUACCUGGU  60
A                                                                 61
```

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
GATAGCGGGT AGCTAGATGC TTAAGCCTCA ATAAAGC                      37
```

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
ACTAGTGAAC CCACTGCTGA TAGCGGGTAG CTAGATG                      37
```